(12) United States Patent
Tsukada et al.

(10) Patent No.: US 6,745,063 B2
(45) Date of Patent: Jun. 1, 2004

(54) BIOMAGNETIC FIELD MEASURING APPARATUS

(75) Inventors: Keiji Tsukada, Kashiwa (JP); Tsuyoshi Miyashita, Fuchu (JP); Akihiko Kandori, Kokubunji (JP); Daisuke Suzuki, Kodaira (JP); Koichi Yokosawa, Kodaira (JP)

(73) Assignee: Hitachi, Ltd., Toyko (JP)

( * ) Notice: Subject to any disclaimer, the term of this patent is extended or adjusted under 35 U.S.C. 154(b) by 4 days.

(21) Appl. No.: 09/940,542

(22) Filed: Aug. 29, 2001

(65) Prior Publication Data

US 2002/0115927 A1 Aug. 22, 2002

(30) Foreign Application Priority Data

Feb. 21, 2001 (JP) ........................................ 2001-044424

(51) Int. Cl.$^7$ ................................................ A61B 5/05
(52) U.S. Cl. ........................ 600/409; 600/481; 600/509; 324/248
(58) Field of Search .................. 600/409, 425, 600/407, 428, 481, 509; 324/244, 248

(56) References Cited

U.S. PATENT DOCUMENTS

| | | | | |
|---|---|---|---|---|
| 3,809,070 A | * | 5/1974 | Doll et al. .................. | 600/409 |
| 4,182,311 A | * | 1/1980 | Seppi et al. ................ | 600/428 |
| 4,690,149 A | * | 9/1987 | Ko ............................. | 600/409 |
| 4,969,469 A | * | 11/1990 | Mills .......................... | 600/409 |
| 6,230,037 B1 | * | 5/2001 | Tsukada et al. ............ | 600/409 |
| 6,370,414 B1 | * | 4/2002 | Robinson .................... | 600/409 |
| 2002/0062076 A1 | * | 5/2002 | Kandori et al. ............. | 600/409 |

FOREIGN PATENT DOCUMENTS

| | | |
|---|---|---|
| JP | 04-141140 | 9/1990 |
| JP | 11-253412 | 3/1998 |

OTHER PUBLICATIONS

T. Miyashita, A. Kandori, K. Tsukada, M. Sato, Y. Terada, H. Horigome, T. Mitsui, "Construction of Tangential Vectors From Normal Cardiac Magnetic Field Components", 20$^{th}$ Annual International Conference—IEEE/EMBS Oct. 29–Nov. 1, 1998, Hong Kong, pp. 520–523.

Keiji Tsukada, Yasuhiro Haruta, Akira Adachi, Hisanao Ogata, Takanori Komuro, Tsuyoshi Ito, Youichi Takada, and Akihiko Kandori, "Multichannel SQUID System Detecting Tangential Components of the Cardiac Magnetic Field", American Institute of Physics, Review of Scientific Instruments, vol. 66, No. 10, Oct. 1995, pp. 5085–5091.

Hidehiro Hosaka and David Cohen, "Part IV Visual Determination of Generators of the Magnetocardiogram", J. Electrocardiology, 9(4) 1976, pp. 426–432.

Naomi Izumida, Yuh Asano, Junro Hosaki, Yasunaga Hiyoshi, Harumizu Sakurada, Takeshi Motomiya, Seiko Kawano, Tohru Sawanobori and Masayasu Hiraoka, "Nondipolarity of Heart Potentials Estimated by Magnetocardiography in Normal Subjects", Jpn Heart J. Nov. 1998, pp. 731–742.

* cited by examiner

*Primary Examiner*—Ruth S. Smith
(74) *Attorney, Agent, or Firm*—Reed Smith LLP; Stanley P. Fisher, Esq; Juan Carlos A. Marquez, Esq

(57) ABSTRACT

A biomagnetic field measuring apparatus includes a plurality of SQUID magneto-meters for measuring a biomagnetic field generated from a living body, living-body signal measuring devices and for measuring and collecting living-body signals generated periodically, an operation processing device for operation processing the biomagnetic field signal and the living-body signal measured simultaneously as pairs in a plurality of directions, and a display unit for displaying a result of the operation processing. Change in time of excitation can be grasped in detail by using a small number of maps without presumption of a magnetic field source and display of many iso-magnetic field maps.

11 Claims, 21 Drawing Sheets

MCG : MAGNETOCARDIOGRAMS

MCG : MAGNETOCARDIOGRAMS

LEFT TEMPORAL MEASUREMENT AREA

RIGHT TEMPORAL MEASUREMENT AREA

BIOMAGNETIC FIELD MEASURING APPARATUS

CROSS-REFERENCE TO RELATED APPLICATIONS

The present invention is relevant to U.S. patent application Ser. No. 09/941,752 being filed by Daisuke Suzuki, Atsushi Ninomiya, Tsuyoshi Miyashita, Akihito Kandori, Keiji Tsukada and Kouich Yokosawa, and assigned to the present assignee, based on Japanese Patent Application No. 2000-334921 filed on Oct. 30, 2000, and is relevant to U.S. patent application Ser. No. 09/940,507 being filed by Kouichi Yokosawa, Daisuke Suzuki, Keiji Tsukada, Tsuyoshi Miyashita and Akihiko Kandori, and assigned to the present assignee, based on Japanese Patent Application No. 2001-044426 filed on Feb. 21, 2001. In particular, the biomagnetic field measuring apparatus of the invention was developed based on the Instrument For Measuring Magnetic Field as disclosed in JP Pat. App. No. 2000-334921, and the SQUID magneto-meters of the invention are based on the Detection Coil-Integrated Gradiometer And Magnetic Field Measuring Instrument as disclosed in JP Pat. App. No. 2001-044426, which are incorporated herein by reference.

BACKGROUND OF THE INVENTION

The present invention relates to a biomagnetic field measuring method and apparatus for measuring a biomagnetic field generated by neural action in a brain, myocardial action in the heart of a living body by means of a plurality of fluxmeters including a high-sensitive superconducting quantum interference device (SQUID).

Heretofore, a measured result of a biomagnetic field is represented by a time changing waveform of measured magnetic field components or an iso-magnetic field map prepared by connecting points where the intensity of the magnetic field at arbitrary time is identical. For example, it is known that Z components ($B_z$) in the orthogonal coordinates or equal-diameter components ($B_r$) in the polar coordinates are measured and values of $B_z$ or $B_r$ are expressed as an iso-magnetic field map (H. Hosaka and D. Cohen, J. Electrocardiol., 9-4, 426 (1976)). Further, it is also known that tangential components ($B_x$, $B_y$) in the orthogonal coordinates are measured to be expressed as an iso-magnetic field map for each component or two-dimensional magnetic field vectors are calculated from $\sqrt{\{(B_x)^2, (B_y)^2\}}$ to be expressed as an iso-magnetic field map (K. Tsukada et al., Review of the Scientific Instruments, 66, 10 (1995)). In addition, a method is known in which normal components $B_z$ are measured and magnetic field components equivalent to tangential components ($B_x$, $B_y$) are analytically calculated from the normal components $B_z$ (T. Miyashita et al., Proceedings 20th International Conference IEEE/EMBS (Hong Kong), 520–523 (1998)).

Heretofore, the analytical result of the biomagnetic field components is represented by using a time waveform of a magnetic field and an iso-magnetic field map. Further, positions, intensities, directions and the like of current sources in a living body at arbitrary time are presumed by solving an inverse problem and these presumed data are used to presume a pre-excited location of arrhythmia in the heart, foci of epilepsy in the brain and the like. In order to trace dynamic phenomena in a certain time zone such as excitation conduction process of myocardium in the heart and neural excitation conduction in the brain, a lot of iso-magnetic field maps at individual time are displayed side by side or loci of vectors of current sources presumed at individual time are represented in a diagram (N. Izumida et al., Japanese Heart Journal, 731–742 (1998)).

SUMMARY OF THE INVENTION

It is an object of the present invention to provide biomagnetic field measuring method and apparatus capable of quantifying conduction process of electro-physiological excitation without presumption of a dipole (magnetic field source) and display of many iso-magnetic field maps.

Without arranging many iso-magnetic field maps side by side to analyze dynamic excitation conduction in the heart and the brain by means of the pattern recognition, a graph or diagram representation for quantifying dynamic excitation conduction without using the pattern recognition is requested. A method of presuming current sources every moment can presume current sources as dipole models when the current sources are positioned locally, while generally the current sources are distributed widely with the spread in many time zones. When the inverse problem is solved every moment, many arithmetic operations are required until the solution is converged. Particularly, when the coincidence of a calculated distribution of magnetic fields prepared by presumed current sources and a distribution of actually measured magnetic fields is bad, presumed values of the current sources are deteriorated. Consequently, when the current sources are presumed every moment in a certain time zone, there is a problem that presumption error is increased to thereby produce an analytical result having interrupted continuity in change of time with respect to positions, intensities and directions of the current sources.

In the present invention, the orthogonal coordinates (x, y, z) (magnetic field components are $B_x$, $B_y$ and $B_y$) and the polar coordinates (r, θ, φ) are used as coordinates in measurement of a biomagnetic field. When an object to be measured is the heart, the orthogonal coordinates employing the chest as an xy plane is used. When an object to be measured is the brain, the polar coordinates (r, θ, φ) (magnetic field components are $B_r$, $B_\theta$ and $B_\phi$) is used since the head has a shape near to a sphere. The magnetic field components (normal components) vertical to the surface of the head are represented by $B_z$ and $B_r$ and components (tangential components) parallel to the plane tangential to the surface of the living body are represented by $B_x$, $B_y$, $B_\theta$ and $B_\phi$.

The following description is made by using the orthogonal coordinates (x, y, z) by way of example, while when the polar coordinates (r, θ, φ) is used, $B_z$, $B_x$ and $B_y$ are to be replaced by $B_r$, $B_\theta$ and $B_\phi$, respectively.

In the biomagnetic field measuring apparatus of the present invention, a set of sensor arrays is used to measure a biomagnetic field in various different directions. At this time, in order to analyze measured results of the biomagnetic field in many directions, (1) simultaneously with measurement of the biomagnetic field in respective directions, any of an electrocardiograph, a phonocardiograph, a polygraph, an electroencephalograph and the like is used as a living-body signal measuring apparatus to measure and collect living-body signals periodically generated except the biomagnetic field signals and including any of waveforms in electrocardiogram, heart sound, polygraph, electroencephalogram and the like as pairs with the biomagnetic field signals, or (2) synchronous signals synchronizing with the start of application of any stimulation signals generated by stimulating a nervous system by electrical stimulation of part of the living body by means of an electric stimulator, by stimulating auditory nerve by generation of sound by means of an auditory stimulator, by stimulating rhinencephalon by generation of smell by means of a smell stimulator, by stimulating visual area by generation of light signal or color signal by means of a visual stimulator, by stimulating tactile nerve by stimulation of skin by means of a touch stimulator or the like are collected as pairs with the biomagnetic field signals in respective directions.

A biomagnetic field (hereinafter referred to as cardiac magnetic field) generated from the heart is measured in two directions on the breast side and the back side or in four directions on the breast side, the back side, the right side and the left side of the chest or heart, for example. It is a matter of course that the biomagnetic field generated from the heart may be measured from different directions other than the above directions.

A biomagnetic field (hereinafter referred to cerebral magnetic field) generated from the head (brain) in response to the above stimulation is measured in two directions on the front side and the rear side of the head or brain or in four directions on the right side and the left side of the front side head and the right side and the left side of the rear side head of the head or the brain or in five directions on the right side and the left side of the front side head, on the right side and the left side of the rear side head and on the top of the head or the brain. It is a matter of course that the biomagnetic field generated from the brain may be measured from different directions other than the above directions.

t is time variable. In the orthogonal coordinates (x, y, z), x and y are coordinates or coordinate position where each sensor constituting the sensor array is disposed and a plane parallel to a plane tangential to the surface of the living body is an xy plane, an axis perpendicular to a plane tangential to the surface of the living body being z.

Waveforms of a biomagnetic field measured in many different directions are subjected to the following processing for each direction. When living-body signals periodically generated are measured and collected as pairs with biomagnetic field signals, a time axis of waveforms $W_m$ (t) (m=1, 2, ..., M) of the living-body signals measured in a plurality of directions of m=1, 2, ..., M is subjected to conversion $T_m$ (m=1, 2, ..., M) so that the time axis of the waveforms $W_m$(t) has a common origin (t=0) where a time variable is t. A time axis of waveforms $F_m$ (m=1, 2, ..., M) of the biomagnetic field signals paired with the living signals $W_m$ (t) is subjected conversion $T_m$ (m=1, 2, ..., M). When the synchronous signals synchronizing with the start of application of a stimulation signal are collected as pairs with the biomagnetic field signals, the time axis of waveforms $F_m$ (m=1, 2, ..., M) of the biomagnetic field signals measured in a plurality of directions of m=1, 2, ..., M is subjected to conversion $T_m'$ (m=1, 2, ..., M) so that the time axis of the waveforms $F_m$ has a common origin (t=0) at times that the synchronous signals are collected. The conversions $T_m$ and $T_m'$ (m=1, 2, ..., M) are conversion that the time axis is moved in parallel.

The waveforms of the biomagnetic field (cardiac magnetic field or cerebral magnetic field) measured in the plurality of directions and having the common origin (t=0) are subjected to the following operation processing.

When a magnetic field component $B_z$ (x, y, t) vertical to the plane tangential to the surface of the living body is measured as the biomagnetic field, a variation $\partial B_z(x, y, t)/\partial x$ in the x direction and a variation $\partial B_z(x, y, t)/\partial y$ in the y direction of the vertical magnetic field component $B_z(x, y, t)$ are calculated and a root sum square, that is, the intensity of a two-dimensional magnetic field vector I (x, y, t) (hereinafter referred to as vector intensity) and the angle θ (x, y, t) thereof are calculated in accordance with equations 1 and 2:

$$I(x, y, t) = \sqrt{\{(\partial B_z(x, y, t)/\partial x)^2 + (\partial B_z(x, y, t)/\partial y)^2\}} \quad (1)$$

$$\theta(x, y, t) = -\tan^{-1}\{(-\partial B_z(x, y, t)/\partial x)/(\partial B_z(x, y, t)/\partial y)\} \quad (2)$$

When tangential components (components parallel to a plane tangential to the surface of the living body) $B_x$ and $B_y$ of a magnetic field generated from the living body is measured, a vector intensity I(x, y, t) and a angle θ (x, y, t) thereof are calculated from a root sum square of the tangential components $B_x$ and $B_y$ in accordance with equations 3 and 4.

$$I(x, y, t) = \sqrt{\{(B_x(x, y, t))^2 + (B_y(x, y, t))^2\}} \quad (3)$$

$$\theta(x, y, t) = -\tan^{-1}\{-B_x(x, y, t)/B_y(x, y, t)\} \quad (4)$$

Next, a maximum vector intensity $I_{max}(x_i, y_j, t)$ and a angle θ $(x_i, y_j, t)$ thereof at individual time of measured biomagnetic field (cardiac magnetic field or cerebral magnetic field) are calculated. The vector intensity I(x, y, t) is maximum at an i-th x coordinate position and a j-th y coordinate position, that is, at a channel (i, j) of the sensor at time t. The calculated maximum vector intensity $I_{max}(x_i, y_j, t)$ and the angle θ $(x_i, y_j, t)$ thereof at individual time t are displayed for a time variable t. This displayed plots are named a time-intensity plot (t-$I_{max}$) and a time-angle plot (t-θ), respectively.

As a result of the above, the time-intensity plot (t-$I_{max}$) and the time-angle plot (T-θ) are obtained from waveforms of the biomagnetic field (cardiac magnetic field or cerebral magnetic field) signals measured in a plurality of directions and having the common origin (t=0). Consequently, the time-intensity (t-$I_{max}$) and the time-angle plot (T-θ) can be displayed for comparison for each measurement side of the biomagnetic field.

Further, positions $(x_i, y_j)$ of all the sensors obtained from waveforms of the biomagnetic field (cardiac magnetic field or cerebral magnetic field) signals measured in a plurality of directions and having the common origin (t=0), that is, the vector intensity I(x, y, t) and the angle (x, y, t) thereof at all the channels can be displayed in the same display screen. This displayed plot is named a time-angle intensity plot (t-. . . I). In this display, the angle .(x, y, t) is plotted for a time variable t and the vector intensity I(x, y, t) is displayed while plotted color, a shade of the plotted color or a magnitude of a plotted mark is changed in accordance with the vector intensity I(x, y, t).

As described above, conduction process of electrophysiological excitation can be quantified and displayed by measuring the cardiac or cerebral magnetic field in the plurality of directions without presumption of a dipole and display of many iso-magnetic field maps.

According to the biomagnetic field measuring apparatus of the present invention, since the vector intensity and the angle thereof are used, conduction process of electrophysiological excitation can be quantified and disease and abnormality for each person can be grasped objectively and quantitatively without presumption of a dipole (magnetic field source) by solving an inverse problem and display of many iso-magnetic field maps.

DESCRIPTION OF THE EMBODIMENTS

Figure 1:
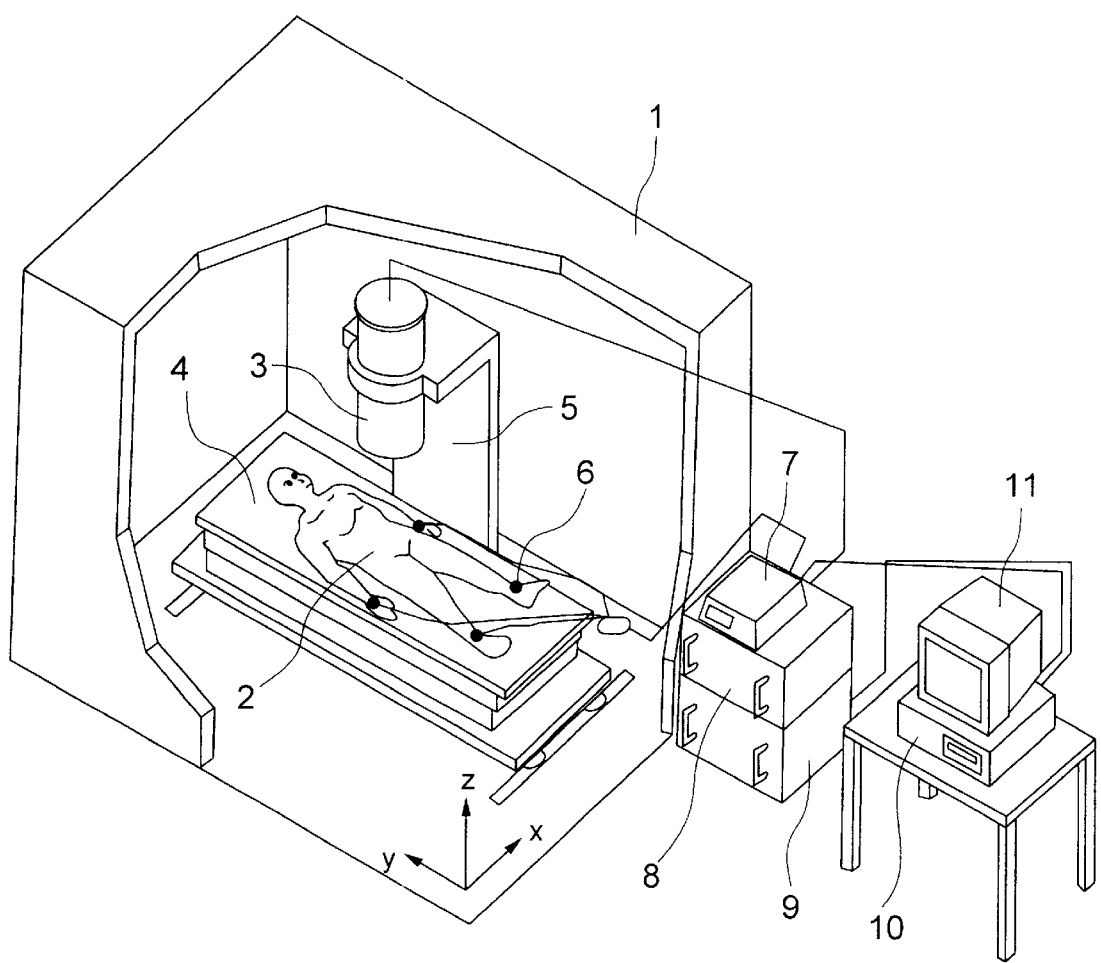
FIG. 1 is a perspective view schematically illustrating a biomagnetic field measuring apparatus according to a first embodiment of the present invention.

A biomagnetic field measuring apparatus according to an embodiment of the present invention measures a biomagnetic field generated from a living body by means of a plurality of SQUID magneto-meters. At this time, a living-body signal measuring apparatus for measuring and collecting living-body signals generated periodically except the biomagnetic field or a stimulator for producing stimulation signals for stimulating any of various nervous systems and synchronous signals synchronizing with the start of application of the simulation signals is used.

Biomagnetic field signals and living-body signals measured and collected as pairs simultaneously in a plurality of directions or biomagnetic field signals measured and collected in a plurality of directions as pairs with the synchronous signals synchronizing with the start of application of the stimulation signals are subjected to operation processing in an operation processing apparatus and the result of the operation processing is displayed on a display unit.

The operation processing apparatus performs time axis conversion for moving a time axis of the biomagnetic field signals measured and collected in the plurality of directions in parallel so that the biomagnetic field signals have a common origin (t=0) and subjects the biomagnetic field signals having the common origin (t=0) to operation processing.

When the living-body signal measuring apparatus is used, waveforms of the living-body signals are subjected to time axis conversion so that a time axis of the waveforms of the living-body signals measured in a plurality of directions has a common origin (t=0) where a time variable is t. At this time, a time axis of waveforms of the biomagnetic field signals paired with the living-body signals is also subjected to the same conversion. When the stimulator is used, a time axis of the biomagnetic field signals measured in the plurality of directions is subjected to time axis conversion so that the time axis has a common origin (t=0) at the time that the synchronous signals are collected.

Further, in another embodiment of the present invention, the operation processing apparatus uses biomagnetic field (cardiac magnetic field or cerebral magnetic field) signals having the common origin (t=0) to calculate intensities and/or angles representing a direction on an xy plane of two-dimensional magnetic field vectors at respective measurement points (x, y) of the biomagnetic field on the assumption that a vertical direction to a plane tangential to the surface of the living body is a z direction and directions perpendicular to the z direction and horizontal to the plane tangential to the surface of the living body are x and y directions. Change in time of the intensities and/or the angles of the two-dimensional magnetic field vectors is displayed on the display unit while using the common origin (t=0) as the origin.

The biomagnetic field measuring apparatus according to another embodiment of the present invention comprises a plurality of SQUID magneto-meters for measuring biomagnetic field (cardiac magnetic field or cerebral magnetic field) signals generated from the heart or the brain of the living body, an operation processing apparatus for performing operation processing of the biomagnetic field signals, and a display unit for displaying the result of the operation processing.

The operation processing apparatus calculates two-dimensional magnetic field vectors at respective measurement points (x, y) of the biomagnetic field from the biomagnetic field signals and calculates the intensity and/or an angle representing a direction on the xy plane of a maximum of the two-dimensional magnetic field vectors at the plurality of measurement points (x, y) at a plurality of times that the biomagnetic field is measured on the assumption that a vertical direction to a plane tangential to the surface of the living body is a z direction and directions orthogonal to the z direction and horizontal to the plane tangential to the surface of the living body are x and y directions. Change in time of the intensity and/or the angle of the maximum two-dimensional magnetic field vector is displayed on the display unit.

In a further embodiment, the intensity and the angle of the two-dimensional magnetic field vectors at the respective measurement points are calculated at a plurality of times that the biomagnetic field is measured. Change in time of the intensities and the angles representing the direction on the xy plane of the two-dimensional magnetic field vectors at respective measurement points (x, y) is displayed in color on the display unit while proportionating the intensities of the two-dimensional magnetic field vectors to a size of plotted points or distinguishing them in color.

Moreover, the biomagnetic field measuring apparatus according to a further embodiment of the present invention comprises a plurality of SQUID magneto-meters for measuring biomagnetic field signals generated from the brain of the living body, a stimulator for producing signals for stimulating the living body and synchronous signals synchronizing with the start of production of the stimulation signals of the living body, an operation processing apparatus for performing operation processing of biomagnetic field (cerebral magnetic field) signals measured in a plurality of directions of the brain of the living body, and a display unit for displaying the result of the operation processing.

The operation processing apparatus performs time axis conversion of waveforms of biomagnetic field (cerebral magnetic field) signals measured in the plurality of directions on the basis of the synchronous signals so that a time axis of the waveforms of the biomagnetic field (cerebral magnetic field) signals has a common origin (t=0) on the assumption that the vertical direction to the plane tangential to the surface of the living body is a z direction, directions orthogonal to the z direction and horizontal to the plane tangential to the surface of the living body are x and y directions, and a time variable is t.

Furthermore, the two-dimensional magnetic field vectors at a plurality of measurement points (x, y) of the biomagnetic field are calculated from the biomagnetic field signals having the common origin (t=0) in the plurality of directions that the biomagnetic field is measured and the intensity and/or the angle representing the direction on the xy plane of a maximum of the two-dimensional magnetic field vectors at the plurality of measurement points (x, y) are calculated at respective points of the time axis having the common origin (t=0) as the origin. Change in time of the intensity and/or the angle of the maximum two-dimensional magnetic field vector are displayed on the display unit in the plurality of directions that the biomagnetic field is measured.

(First Embodiment)

FIG. 1 is a perspective view schematically illustrating a biomagnetic field measuring apparatus according to a first embodiment of the present invention. The biomagnetic field measuring apparatus for measuring a magnetic field (cardiac magnetic field) generated from the heart (hereinafter referred to as cardiac magnetic field measurement) uses a plurality of magnetic sensors constituted by superconducting interference devices (SQUID). In order to remove influence of circumstance magnetic noise, the cardiac magnetic field measurement is performed within a magnetically shielded room 1. A subject 2 to be measured is lying on a bed 4.

The orthogonal coordinates (x, y, z) are set up so that its xy plane is equal to the surface of the bed. Disposed above the subject 2 is a dewar 3 including a plurality of magnetic sensors having the SQUIDs and detection coils connected to the SQUIDs structured integrally and filled with liquid He. The dewar 3 is fixedly mounted on a floor by means of a gantry 5. Outputs of the magnetic sensors are supplied to an FLL (Flux Locked Loop) circuit 8 which produces voltages proportional to the intensity of the magnetic fields detected by the detection coils.

The FFL circuit 8 cancels change of a biomagnetic field supplied to the SQUIDs by means of feedback coils so that outputs of the SQUIDs are maintained to be fixed. A current flowing through the feedback coil is converted into a voltage to thereby obtain a voltage output proportional to change of a biomagnetic field signal. The voltage output is amplified by an amplifier of an amplifier-filter circuit 9 and a frequency band thereof is selected by a filter circuit. The voltage output subjected to the selection of the frequency band is A/D converted and recorded as data in a data acquisition and analysis apparatus (operation processing apparatus).

The data acquisition and analysis apparatus 10 performs varieties of operation processing and displays the result of the operation processing on a display 11. Further, the result is outputted by means of a printer. The data acquisition and analysis apparatus 10 also performs measurement of electrocardiogram simultaneously with cardiac magnetic field measurement. Electrodes 6 for electrocardiograph are stuck on wrists and ankles of the subject 2 and electric potentials are led to an electrocardiograph 7 by limb lead. An output of the electrocardiograph 7 is supplied to the amplifier-filter circuit 9 of the biomagnetic field measuring apparatus to be subjected to amplification and frequency band selection and is operation processed in the same manner as the cardiac magnetic field, so that waveform in electrocardiogram is displayed on the display 11. When the cardiac magnetic field measurement is performed on the front and the back of the subject, the subject lies with the face upward and downward, respectively, to measure the cardiac magnetic field.

Figure 2:
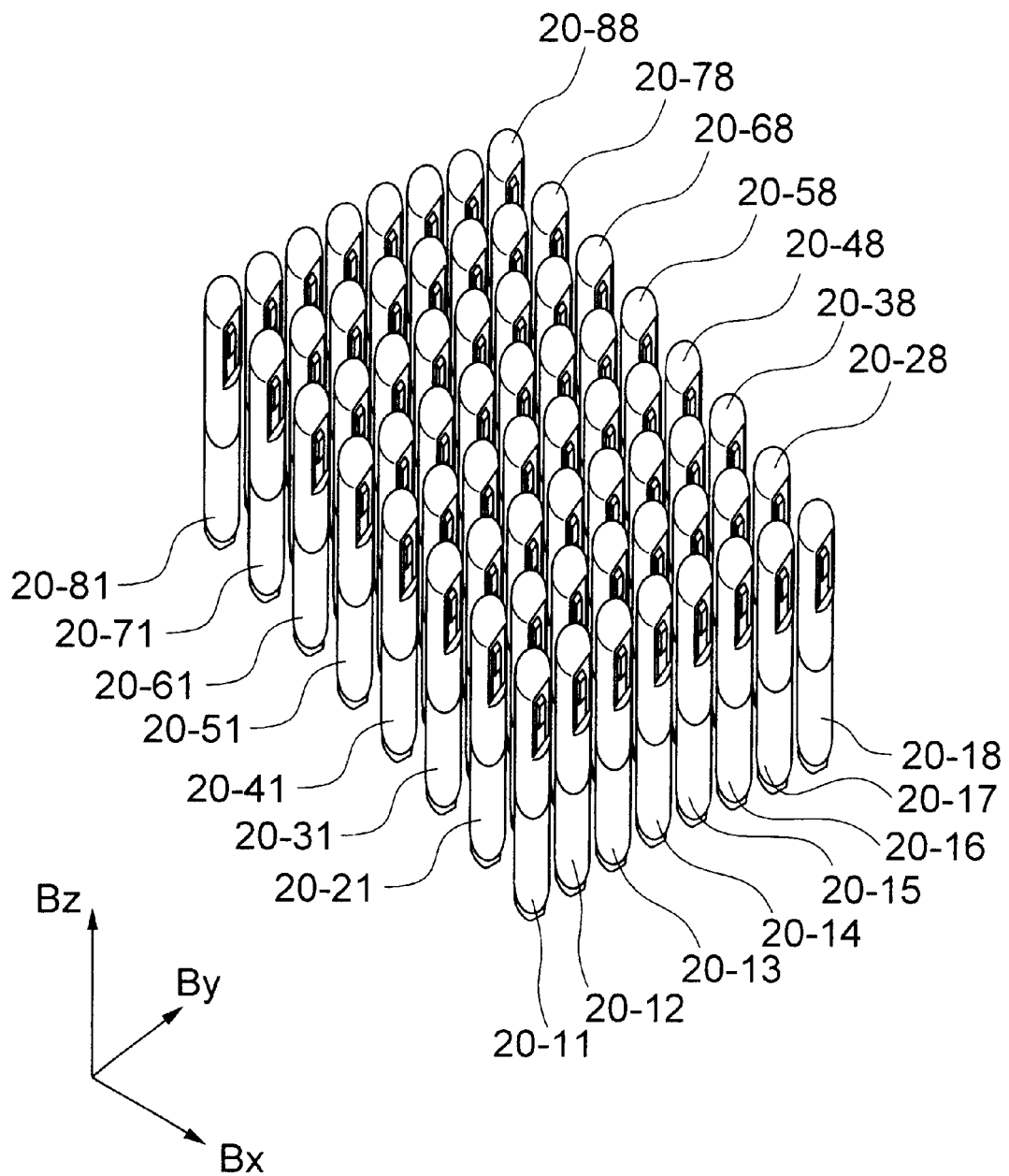
FIG. 2 is a perspective view illustrating an arrangement of magnetic sensors in the first embodiment of the present invention.

FIG. 2 is a perspective view for explaining an arrangement of the magnetic sensors in the first embodiment of the present invention. The coil for detecting a normal component of the biomagnetic field has a plane vertical to the z direction. The magnetic sensors 20-i (i=11, 12, ... , 18; i=21, 22, ... , 28; i=31, 32, ... , 38; i=41, 42, ... , 48; i=51, 52, ... , 58, i=61, 62, ... , 68; i=71, 72, ... , 78, i=81, 82, ... , 88) are disposed vertically in a standing posture on the bottom of the dewar. The magnetic sensors are disposed at equal spaces (25 mm) in the x and y directions so as to detect a variation in the x and y directions of the normal component of the biomagnetic field exactly. Eight sensors are arranged in each of the x and y directions to be formed into a square lattice and have 64 channels.

Figure 3:
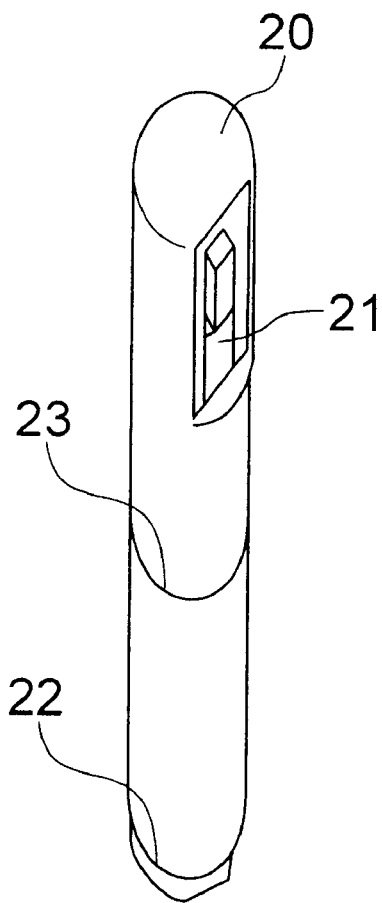
FIG. 3 is a perspective view schematically illustrating the magnetic sensor for detecting a normal component of a biomagnetic field in the first embodiment of the present invention.
Figure 3:
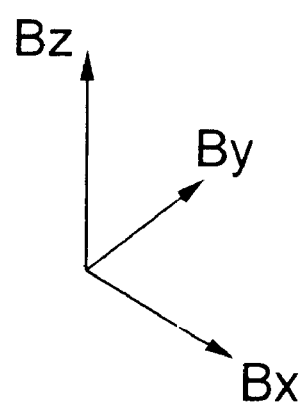

FIG. 3 is a perspective view schematically illustrating the magnetic sensor for detecting the normal component of the biomagnetic field in the first embodiment of the present invention. The magnetic sensor 20 is a sensor for measuring a vertical component $B_z$ to the surface of the body and a coil thereof made of superconducting wire (Nb—Ti wire) has a vertical plane to the z direction. The coil is constituted of a combination of two reverse coils including a detection coil 22 disposed near to the living body and a reference coil 23 for removing external magnetic noise to form a linear differential coil. A coil diameter of the detection coil 22 and the reference coil 23 is 20 mm and a distance (baseline) between the detection coil 22 and the reference coil 23 is 50 mm.

External magnetic noise is produced from a signal source distant from the living body and similarly detected by the detection coil 22 and the reference coil 23. On the other hand, a magnetic field source within the living body is near to the coils and accordingly a biomagnetic field is detected stronger or larger by the detection coil 22. The detection coil 22 detects both of a biomagnetic field signal and external magnetic noise and the reference coil 23 detects only external magnetic noise. Accordingly, measurement having large S/N can be performed on the basis of a difference of the magnetic fields detected by both the coils. The linear differential coil is connected to an input coil of the SQUID through a superconducting wire on a mounting board in which the SQUID 21 is mounted and the biomagnetic field signal detected by the coil is supplied to the SQUID.

The dewar including the magnetic sensors is disposed above the subject lying on the bed to measure a cardiac magnetic field generated from the heart thereof. In this connection, a direction of an axis of the body is assumed to be y axis and a direction to perpendicular to the y axis be the x axis.

Figure 4:
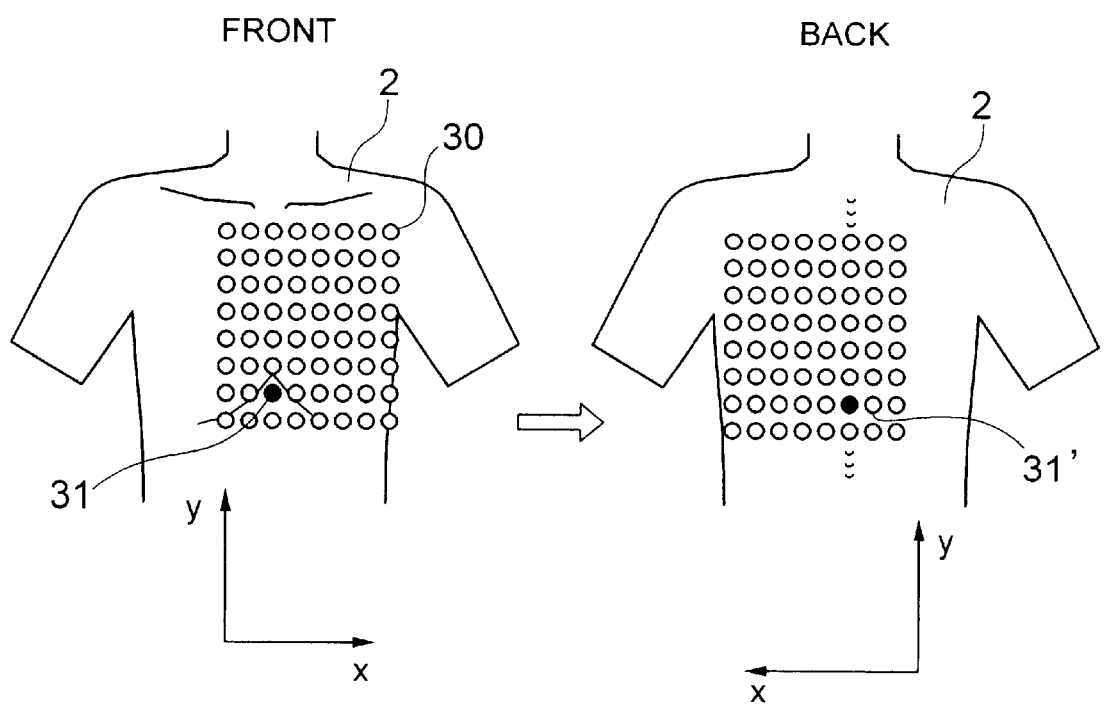
FIG. 4 illustrates a positional relation of an arrangement of the magnetic sensors and the front and the back of the breast of a human body in the first embodiment of the present invention.

FIG. 4 illustrates a positional relation of an arrangement of the magnetic sensors and the front and the back of the breast of the subject 2 in the first embodiment of the present invention. In FIG. 4, circles represent positions where the magnetic sensors are arranged into the array of 8×8, that is, measurement points 30 of the magnetic field. A measurement reference point 31 on the front and a measurement reference point 31' on the back of the breast of the subject 2 are the same point on the xy coordinates. In the example shown in FIG. 4, the measurement reference point 31 on the front corresponds to a magnetic sensor positioned at the second row from the bottom and the third column from the left and the measurement reference point on the back corresponds to a magnetic sensor positioned at the second row from the bottom and the sixth column from the left. However, the coordinate system on the back is reverse to the coordinate system on the front. For example, a magnetic sensor positioned at the first row and the first column on the front corresponds to a magnetic sensor positioned at the first row and the eighth column on the back and a magnetic sensor positioned at the eighth row and eighth column on the front correspond to a magnetic sensor positioned at the eighth row and the first column on the back.

Figure 5:
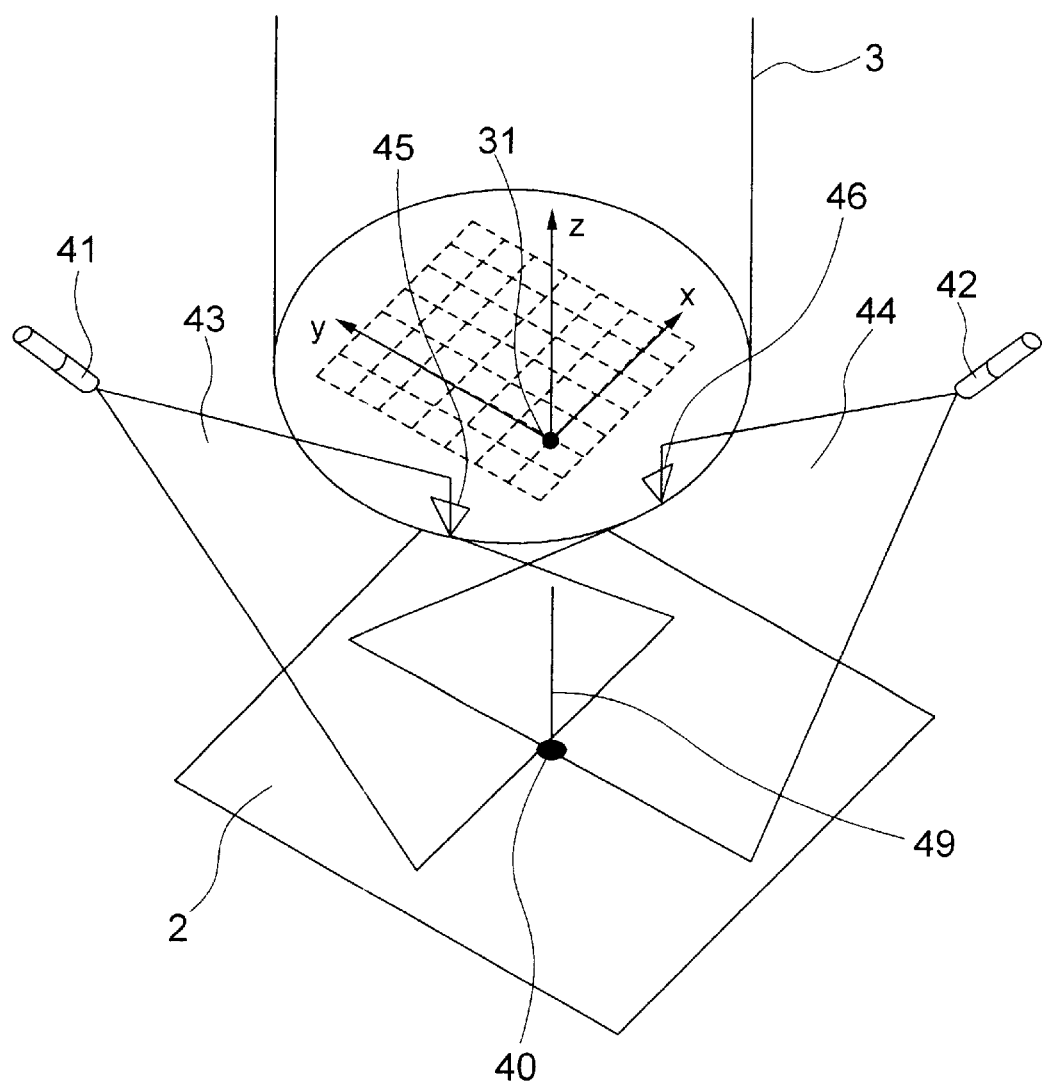
FIG. 5 is a perspective view for explaining a method of aligning an arrangement of the magnetic sensors and the breast of the human body in the first embodiment of the present invention.

FIG. 5 is a perspective view for explaining a method of aligning the arrangement of the magnetic sensors and the breast of the human body in the first embodiment of the present invention. Various mechanisms and methods of aligning the measurement reference point 31 of the sensor array and a reference point 40 of the subject are known. In the example shown in FIG. 5, an x-direction laser light source 41 for generating an x-axis line forming beam 43 spreading into a fan within a plane parallel to the xz plane of the orthogonal coordinates and a y-direction laser light source 42 for generating a y-axis line forming beam 44 spreading in a fan within a plane parallel to the yz plane of the orthogonal coordinates are used for the alignment. An xz mark 45 indicating a position of the xz plane of the orthogonal coordinates and a yz mark 46 indicating a position of the yz plane of the orthogonal coordinates are marked on an outer peripheral surface of the dewar 3.

A position of the x-direction laser light source 41 is adjusted so that the outer peripheral surfaces of the subject 2 and the dewar 2 are irradiated with the x-axis line forming beam 43 and the reference point 40 set up on the surface of the subject and the xz mark 45 on the dewar 3 are irradiated with the beam 43. Similarly, a position of the y-direction laser light source 42 is adjusted so that the outer peripheral surfaces of the subject 2 and the dewar 2 are irradiated with the y-axis line forming beam 44 and the reference point 40 set up on the surface of the subject and the yz mark 46 on the dewar 3 are irradiated with the beam 44. In this manner, the positions of the sensors and the living body can be adjusted. The beams 43 and 44 cross each other to form a cross line 49 parallel to the z axis.

Figure 6:
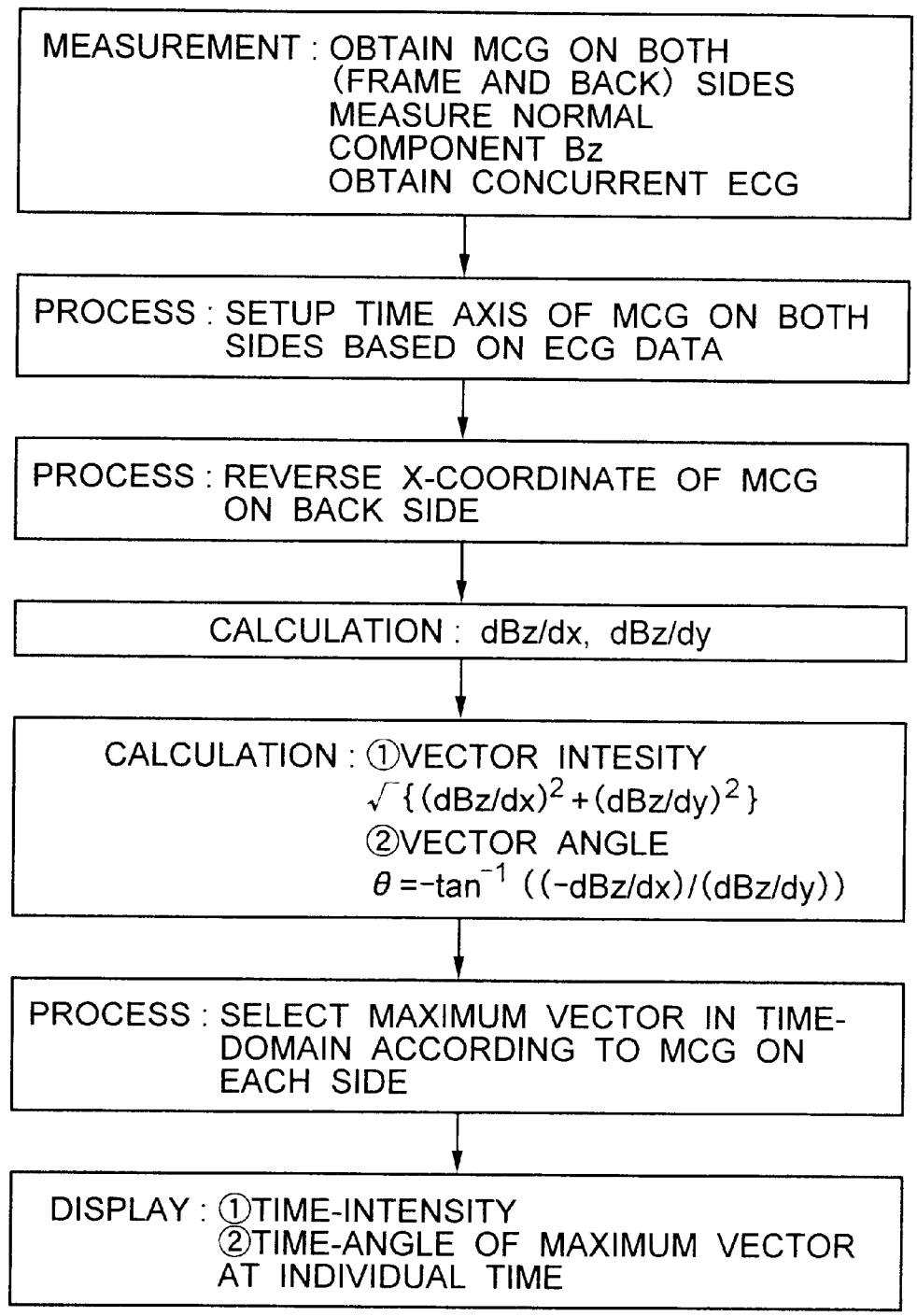
FIG. 6 is a flow chart showing measurement processing of a biomagnetic field and analyzation processing of measured signals in the first embodiment of the present invention.

FIG. 6 is a flow chart showing measurement processing of a biomagnetic field and analyzation processing of measured signals in the first embodiment of the present invention. In the analyzation shown in FIG. 6, a maximum vector at individual time of a measured cardiac magnetic field is selected. First, the cardiac magnetic field measurement is performed in two directions on both the front and the back sides. A normal component $B_z$ of the cardiac magnetic field is measured. An electrocardiogram is also measured simultaneously with the cardiac magnetic field measurement. Next, the waveforms in electrocardiogram measured simultaneously with the cardiac magnetic field measurement on the front and the back are adjusted in the time axis so that the waveforms in electrocardiogram have the same waveform at the same time. That is, the time axis of respective electrocardiograms is moved in parallel so that the same time and angle at the respective electrocardiograms measured become the same time. The parallel movement of the time axis adjusted on the respective electrocardiograms is also applied to measured data of the cardiac magnetic field corresponding to the measurement of the waveform in electrocardiogram, so that setting of the time axis of measured data of the cardiac magnetic field (hereinafter referred to as cardiac magnetic field waveform) is made on the basis of electrocardiogram data.

As illustrated in FIG. 4, in order to cause the measured data of the cardiac magnetic field on the front to correspond to that on the back, the x-coordinate on the back is reversed to change correspondence of the position of the sensor array and the measured data. Next, a variation $\partial B_z(x, y, t)/\partial x$ in the x direction and a variation $\partial B_z(x, y, t)/\partial y$ in the y direction of a measured magnetic field component $B_z (x, y, t)$ vertical to the surface of the living body are calculated. The vector intensities $I(x, y, t)$ and the vector angle $\theta (x, y, t)$ at the 64 measurement points measured on each of the front and the back are calculated on the basis of the equation 1 and the equation 2, respectively.

Next, a maximum vector of the vector intensities $I(x, y, t)$ at the measurement points at individual time t on each measurement side (front and back) of the cardiac magnetic field is extracted. That is, the maximum vector intensity $I_{max}$ $(x_i, y_j, t)$ and the angle $\theta (x_i, y_j, t)$ thereof at individual time t of the vector intensities $I(x, y, t)$ calculated from the measured data of the cardiac magnetic fields on the front and the back are calculated. Then, the calculated maximum vector intensity $I_{max} (x_i, y_j, t)$ and the angle $\theta (x_i, y_j, t)$ thereof at individual time t are displayed with respect to the time variable t. In other words, a time-intensity plot (t-$I_{max}$) and a time-angle plot (T-$\theta$) on each measurement side (front and back) of the cardiac magnetic field are displayed. A definite example obtained on the basis of the flow chart of FIG. 6 is now described.

Figure 7:
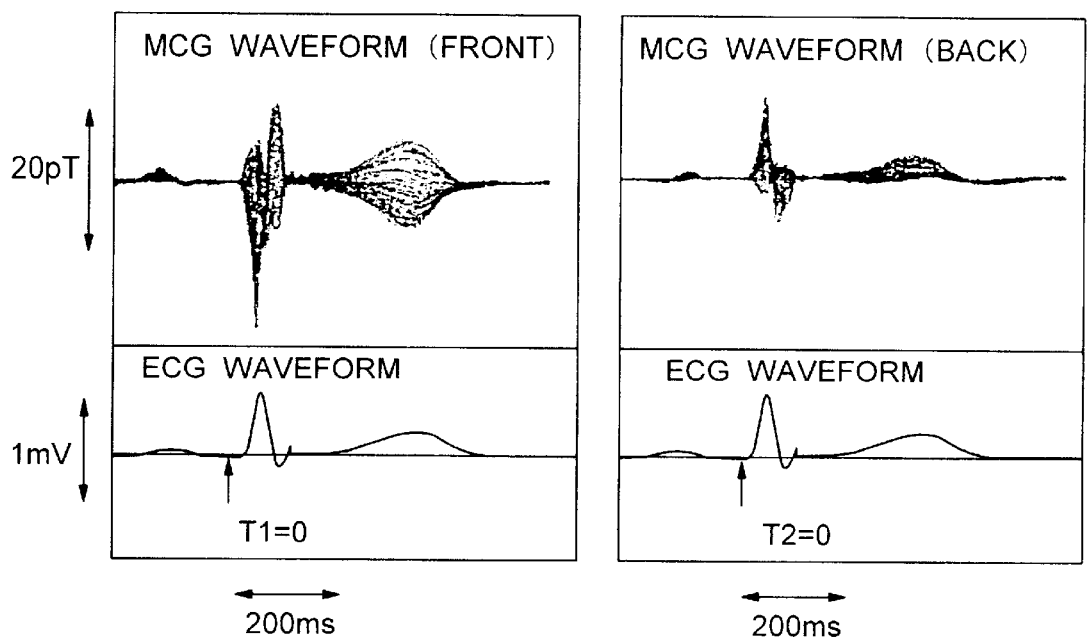
FIG. 7 is a diagram showing an example of waveforms of a cardiac magnetic field measured on the front and the back of a normal subject being a subject to be measured and waveforms in electrocardiogram measured simultaneously with the measurement of the cardiac magnetic field waveforms in the first embodiment of the present invention.

FIG. 7 is a diagram showing an example of waveforms of cardiac magnetic fields measured on the front and the back of a normal subject as the subject and waveforms in electrocardiograms measured simultaneously with the measurement of the waveforms of cardiac magnetic fields. In FIG. 7, the waveforms of cardiac magnetic fields are displayed by overlapping all time waveforms of 64 channels and the waveforms in electrocardiograms indicate waveforms of the lead II. In order to adjust the time axis of the waveforms of cardiac magnetic fields measured on the front and the back, time T1 at a start point of a time zone, in which ventricle is depolarized, named the QRS complex of the waveform in electrocardiogram measured in the cardiac magnetic field measurement on the front is set to 0. Then, time T2 at a start point of the QRS complex of the waveform in electrocardiogram measured in the cardiac magnetic field measurement on the back is set to 0, so that the time axes of the two waveforms in electrocardiograms are matched. The origin of time of the waveform in electrocardiogram on the front is set to t=T1=0 and the origin of time of the waveform in electrocardiogram on the back is set to t=T2=0.

Figure 8:
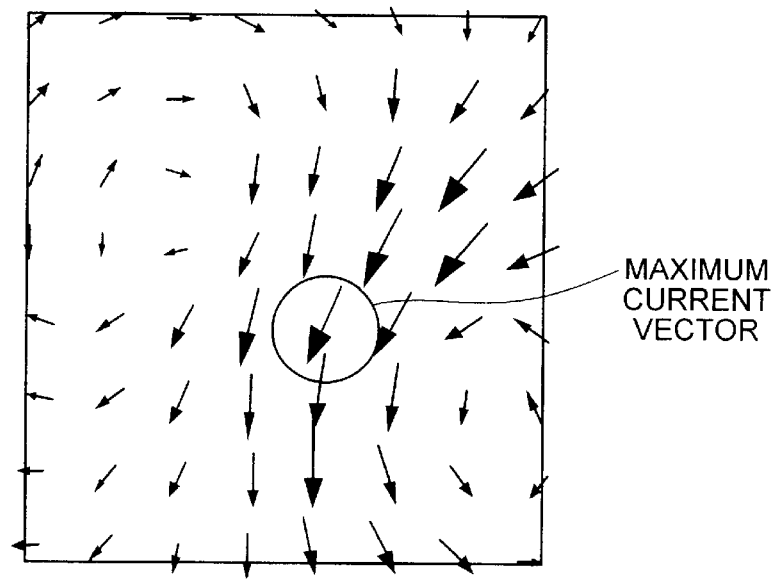
FIG. 8 is a diagram showing a current arrow map and a maximum current vector at the time reached after the elapse of 30 ms from a start point of a QRS complex of the waveform in cardiac magnetic fields of the normal subject measured on the front in the first embodiment of the present invention.

FIG. 8 is a diagram showing a current arrow map and a maximum current vector at the time reached after the elapse of 30 ms from the start point of the QRS complex in the process that the ventricle is depolarized, of the waveform in cardiac magnetic field of the normal subject measured on the front in the first embodiment of the present invention. The intensities of respective arrows at 64 measurement points represent the intensity of vectors based on the equation 1 and the angle is calculated on the basis of the equation 2. A largest vector among 64 vectors is selected as a maximum vector.

Figure 9:
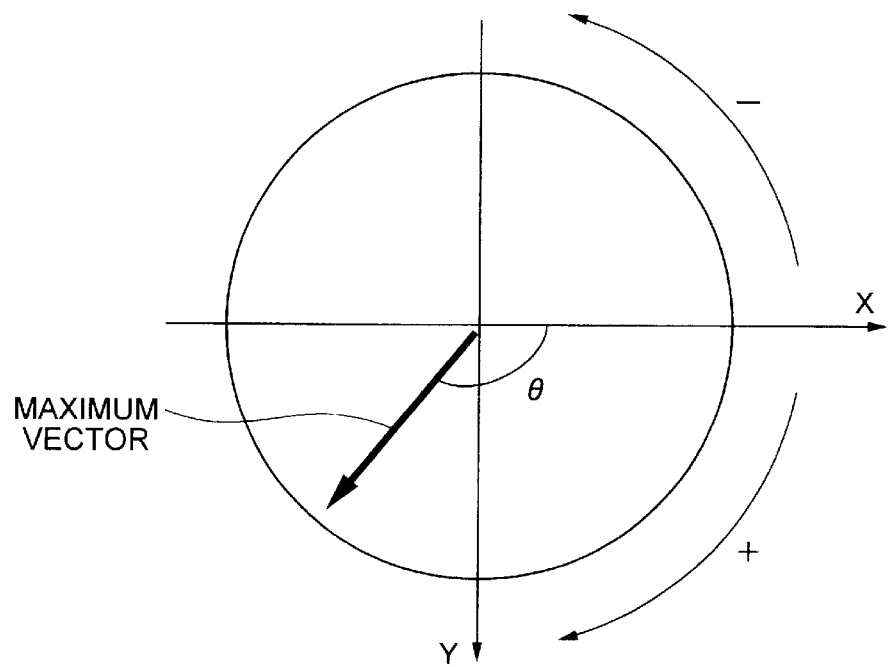
FIG. 9 is a diagram showing a reference of a angle of the maximum vector in the first embodiment of the present invention.

FIG. 9 is a diagram showing a reference of a angle $\theta$ of the maximum vector in the first embodiment of the present invention. In FIG. 9, the positive direction (right direction) of the x axis is assumed to be $\theta$=0 degree, a clockwise direction be a positive direction of the angle and a counterclockwise direction be a negative direction of the angle.

Figure 10:
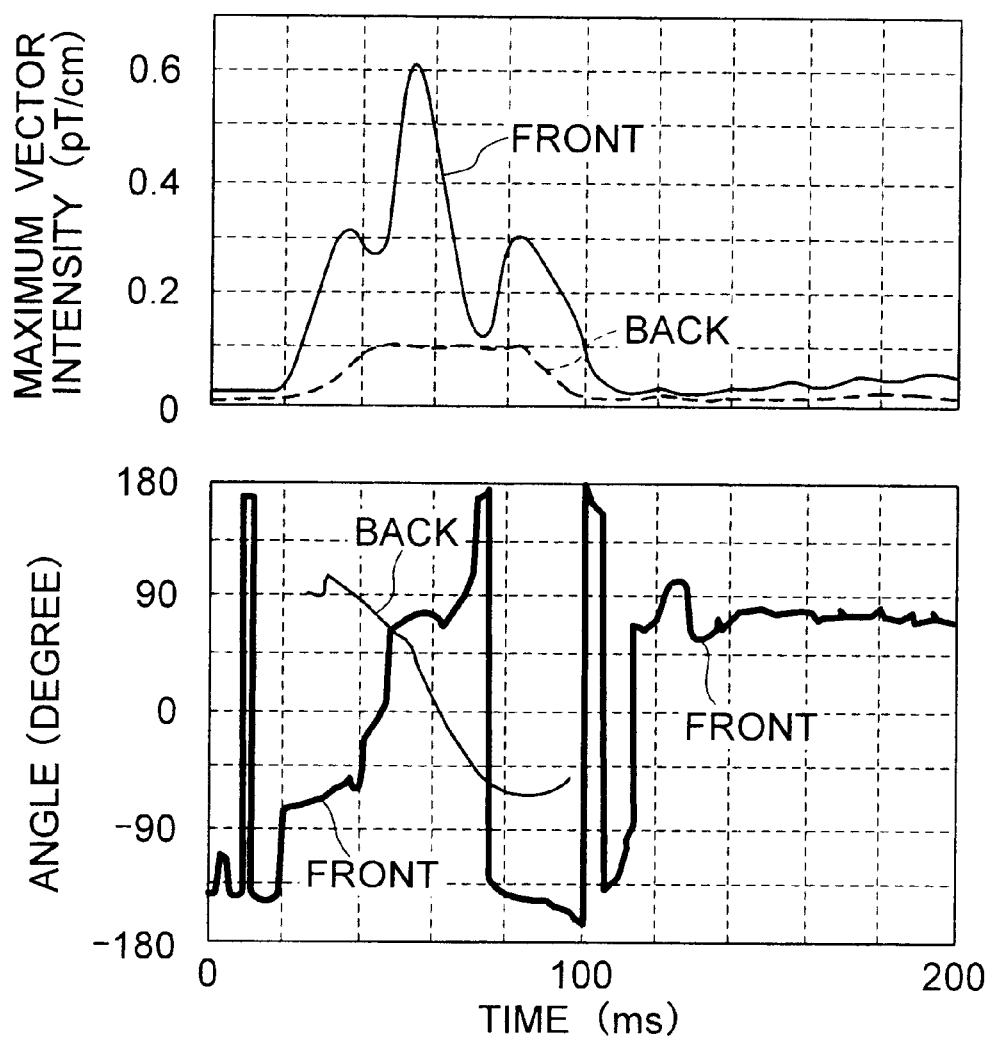
FIG. 10 is a diagram showing a display example of a time-intensity plot (t-$I_{max}$) and a time-angle plot (t-$\theta$) in a time zone until 200 ms from the start point of the QRS complex of the cardiac magnetic field waveforms of the normal subject measured on the front and the back in the first embodiment of the present invention.

FIG. 10 is a diagram showing a display example of a time-intensity plot (t-$I_{max}$) and a time-angle plot (t-$\theta$) in the time zone until 200 ms from the start point of the QRS complex in the process that the ventricle is depolarized, of the cardiac magnetic field waveform of the normal subject measured on the front and the back in the first embodiment of the present invention. A maximum vector intensity (pT/cm) obtained from the cardiac magnetic field waveform measured on the front and the back and change in time of the angle have different patterns. However, the maximum vector intensity (pT/cm) is common in that it exhibits a pattern that values thereof are large in the time zone from about 20 ms befind the start point of the QRS complex until about 100 ms.

Next, a measurement example relative to a patient having a right bundle branch block of bundle branch blocks that a ventricle has conduction block is described.

Figure 11:
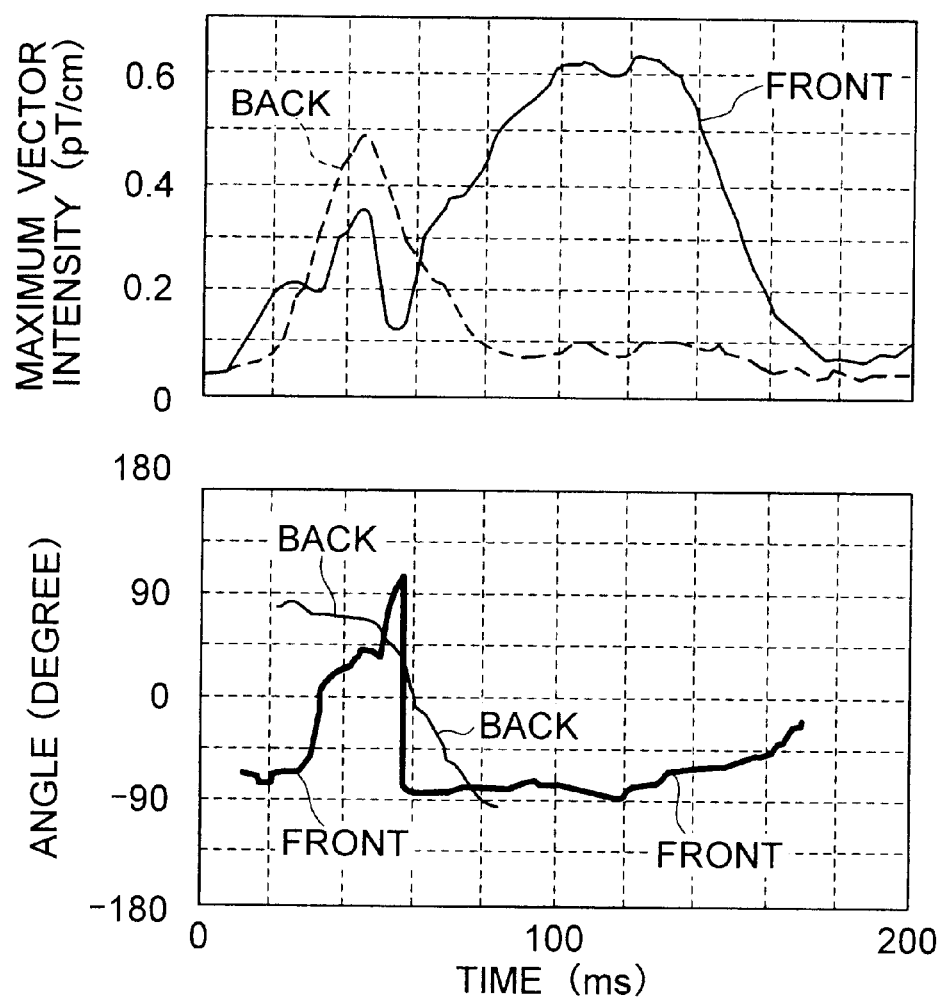
FIG. 11 is a diagram showing a display example of a time-intensity plot (t-$I_{max}$) and a time-angle plot (t-$\theta$) in the time zone until 200 ms from the start point of the QRS complex of the cardiac magnetic field waveforms of a patient having a right bundle branch block measured on the front and the back in the first embodiment of the present invention.

FIG. 11 is a diagram showing a display example of a time-intensity plot (t-$I_{max}$) and a time-angle plot (t-$\theta$) in the time zone until 200 ms from the start point of the QRS complex in the process that the ventricle is depolarized, of the cardiac magnetic field waveform of a patient having a right bundle branch block measured on the front and the back in the first embodiment of the present invention. Differently from the result in case of the normal subject shown in FIG. 10, it is understood that the vector intensity obtained from the cardiac magnetic field waveform measured on the front has a large value over a long time zone from after the elapse of about 60 ms from the start point of the QRS complex until about 160 ms and an active time of the heart is long. As compared with change in time of the angle obtained from the cardiac magnetic field waveform measured on the front with that in case of the normal subject shown in FIG. 10, it is understood that change in the initial time zone starting from the start point of the QRS complex is small as compared with the case of the normal subject. As described above, abnormality in excitation conduction of the heart can be judged easily by the present invention.

(Second Embodiment)

In the second embodiment, all cardiac magnetic field waveform data of 64 channels are displayed in addition to the display of the time-intensity plot (t-$I_{max}$) and the time-angle plot (t-$\theta$) on both the measurement sides (front and back) of the cardiac magnetic field.

Figure 12:
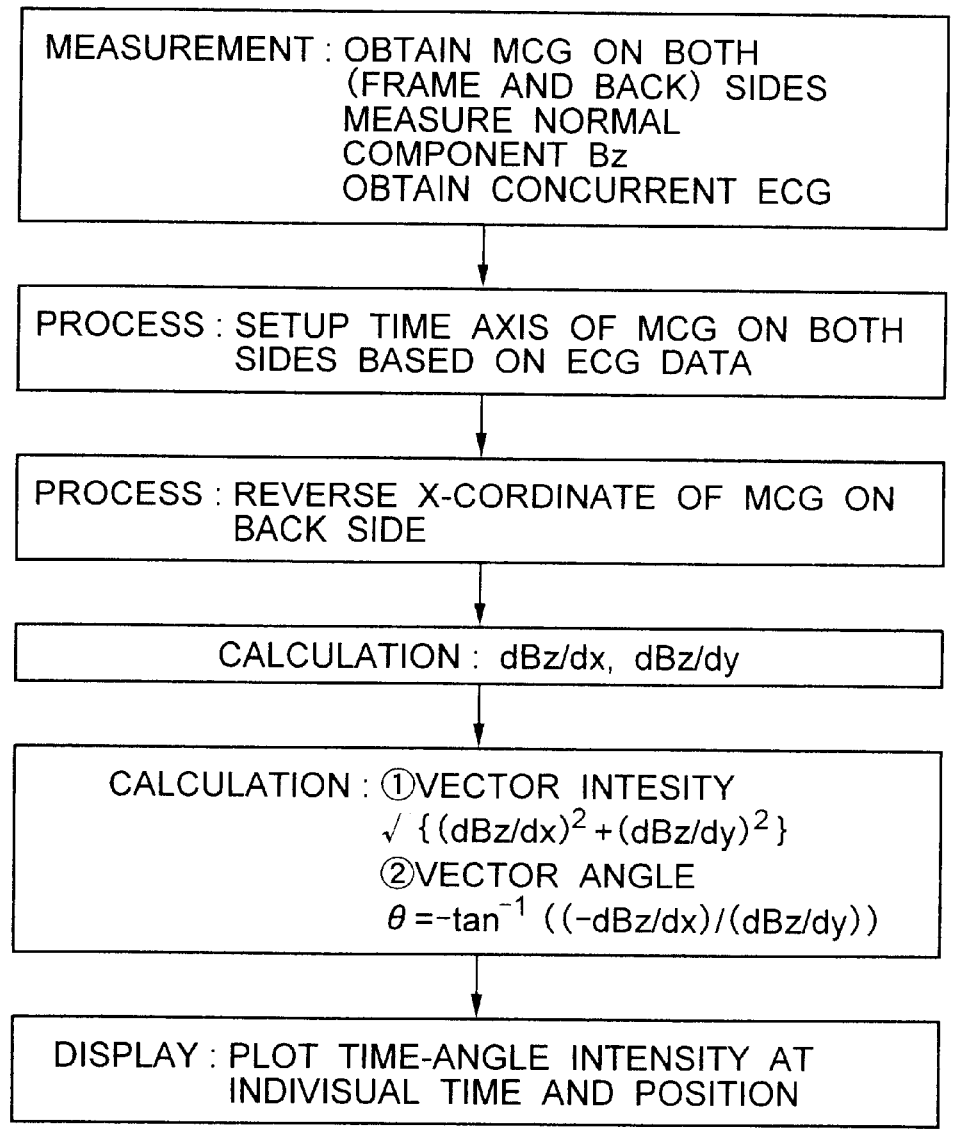
FIG. 12 is a flow chart showing measurement processing of the biomagnetic field and analyzation processing of measured signals in case where a time-angle·intensity plot of vectors at individual time of all of 64 channels is prepared in a second embodiment of the present invention.

FIG. 12 is a flow chart showing measurement processing of the biomagnetic field and analysis process of measured signals in case where a time-angle·intensity plot (t-$\theta$·I) of vectors at individual time of all of 64 channels is prepared in the second embodiment of the present invention. In the flow chart shown in FIG. 12, operation until the processing for calculating the vector intensity and the angle thereof at respective measurement points (channels) is performed is the same as that of FIG. 6. In the flow chart shown in FIG. 12, the time-angle-intensity plot (t-θ·I) of the vectors at all of 64 channels obtained from the cardiac magnetic field data measured on the front and the back is displayed as it is without selection of the maximum vector.

Figure 13:
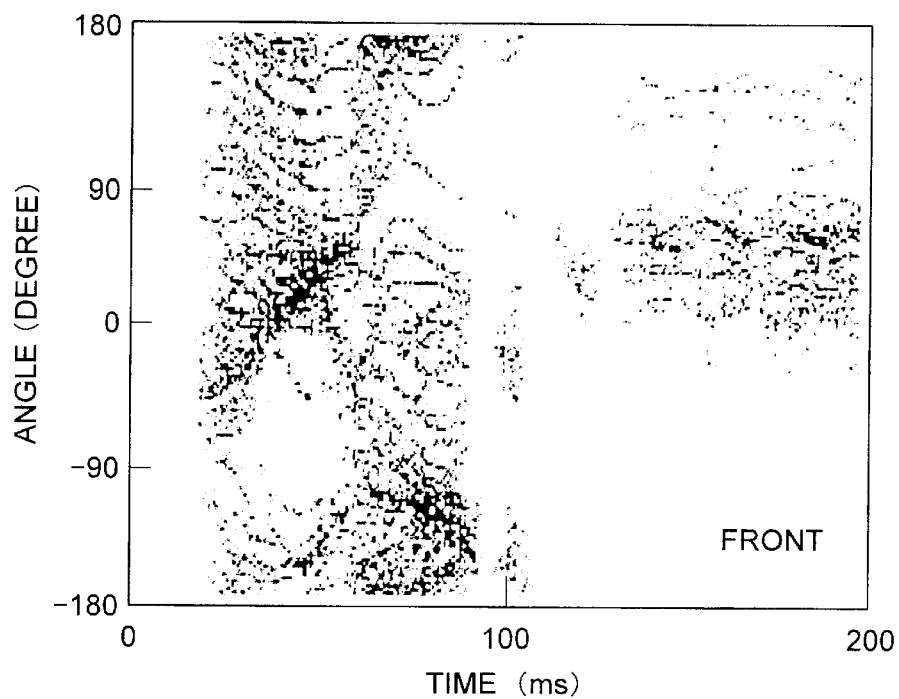
FIG. 13 is a diagram showing a display example of a time-angle intensity plot of vectors of all of 64 channels in the time zone until 200 ms from the start point of the QRS complex of the cardiac magnetic field waveforms measured on the front of the normal subject in the second embodiment of the present invention.

FIG. 13 is a diagram showing a display example of a time-angle-intensity plot of vectors of all of 64 channels in the time zone until 200 ms from the start point of the QRS complex in the process that the ventricle is depolarized, of the cardiac magnetic field waveforms measured on the front of the normal subject in the second embodiment of the present invention.

Figure 14:
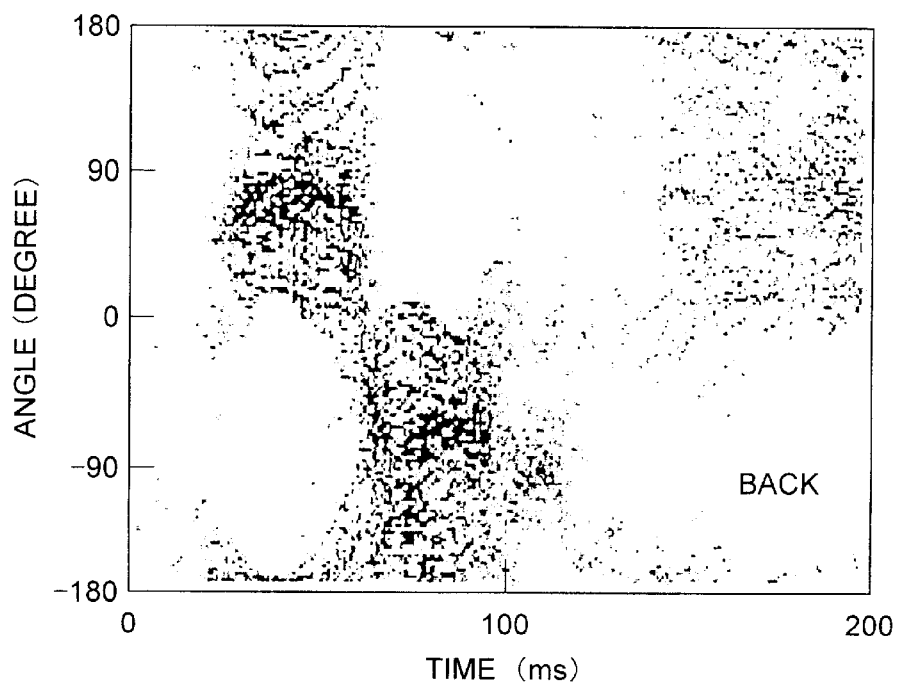
FIG. 14 is a diagram showing a display example of a time-angle·intensity plot of vectors of all of 64 channels in the time zone until 200 ms from the start point of the QRS complex of the cardiac magnetic field waveforms measured on the back of the normal subject in the second embodiment of the present invention.

FIG. 14 is a diagram showing a display example of a time-angle-intensity plot of vectors of all of 64 channels in the time zone until 200 ms from the start point of the QRS complex in the process that the ventricle is depolarized, of the cardiac magnetic field waveforms measured on the back of the normal subject in the second embodiment of the present invention.

Figure 15:
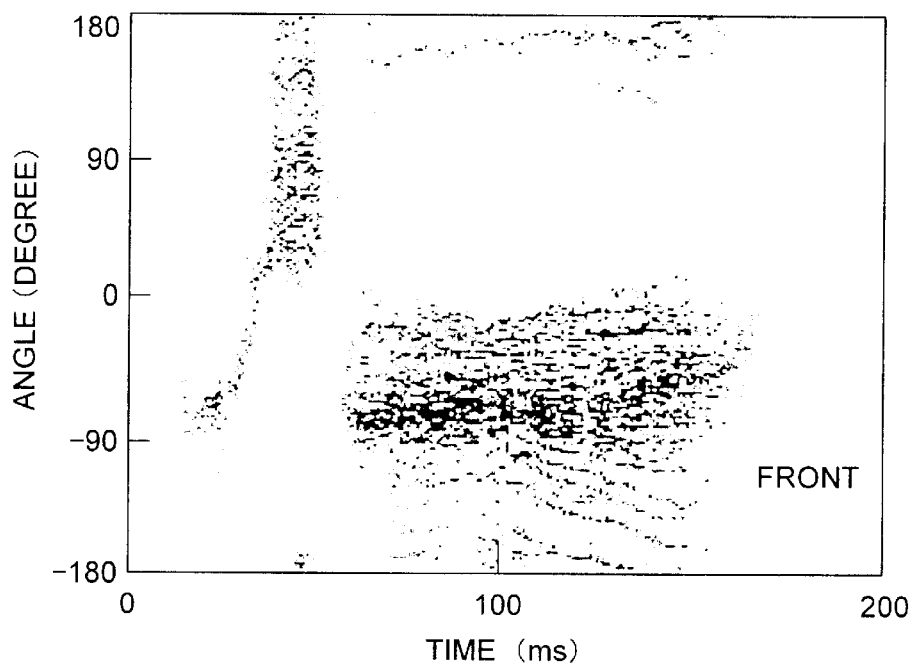
FIG. 15 is a diagram showing a display example of a time-angle·intensity plot of vectors of all of 64 channels in the time zone until 200 ms from the start point of the QRS complex of the cardiac magnetic field waveforms of a patient having right bundle branch block measured on the front in the second embodiment of the present invention.

FIG. 15 is a diagram showing a display example of a time-angle-intensity plot of vectors of all of 64 channels in the time zone until 200 ms from the start point of the QRS complex in the process that the ventricle is depolarized, of the cardiac magnetic field waveforms of a patient having right bundle branch block measured on the front in the second embodiment of the present invention. It is recognized at a glance that the pattern of the plot of FIG. 15 is greatly different from that of FIG. 13.

Figure 16:
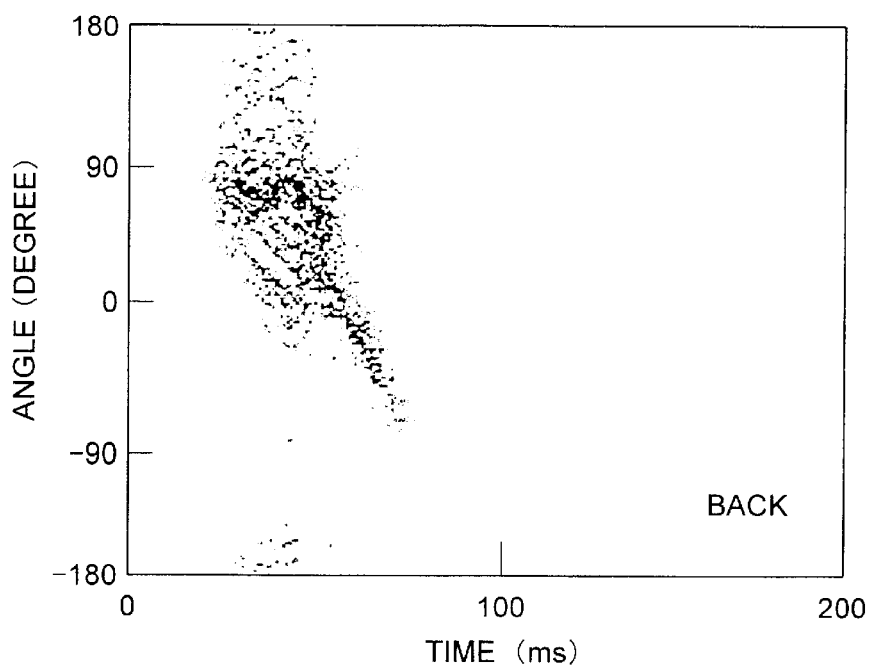
FIG. 16 is a diagram showing a display example of a time-angle·intensity plot of vectors of all of 64 channels in the time zone until 200 ms from the start point of the QRS complex of the cardiac magnetic field waveforms of a patient having right bundle branch block measured on the back in the second embodiment of the present invention.

FIG. 16 is a diagram showing a display example of a time-angle-intensity plot of vectors of all of 64 channels in the time zone until 200 ms from the start point of the QRS complex in the process that the ventricle is depolarized, of the cardiac magnetic field waveforms of a patient having right bundle branch block measured on the back in the second embodiment of the present invention. It is recognized at a glance that the pattern of the plot of FIG. 16 is greatly different from that of FIG. 14.

In FIGS. 13 to 16, since the vector intensities at 64 measurement points at individual time are distinguished by density of plotted points and the angle is displayed as the ordinate axis, difference in the displayed pattern can be identified easily. The vector intensities may be displayed by colored plotted points (color scale) or by the magnitude of plotted points instead of being displayed by the density of the plotted points. With such plotting, difference from the normal subject can be detected easily.

(Third Embodiment)

In the third embodiment, magnetic field components in the x and y directions of the biomagnetic field are measured.

Figure 17:
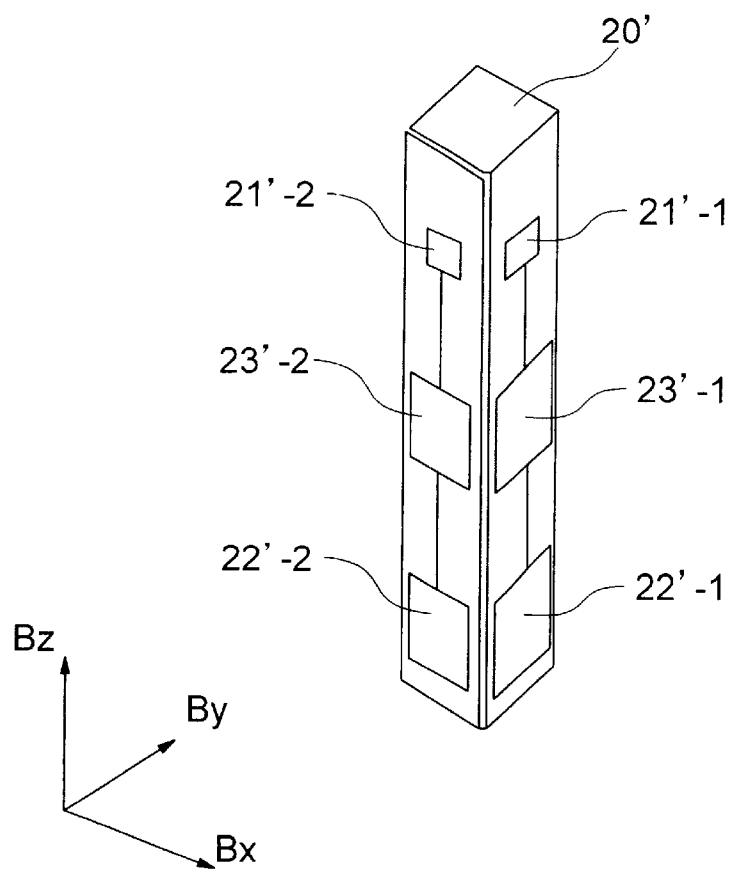
FIG. 17 is a diagram schematically illustrating an example of a magnetic sensor for detecting tangential components $B_x$ and $B_y$ of the biomagnetic field used in a third embodiment of the present invention.

FIG. 17 is a diagram schematically illustrating an example of a magnetic sensor for detecting tangential components $B_x$ and $B_y$ of the biomagnetic field used in the third embodiment of the present invention. The magnetic sensors 20' shown in FIG. 17 use a planar type coil.

The sensor for measuring a magnetic field in the x direction includes a detection coil 22'-1 and a reference coil 23'-1 arranged side by side on one plane to form a linear differential coil for measuring the magnetic field in the x direction. The detection coil 22'-1 and the reference coil 23'-1 have a regular square of 20 mm×20 mm and a distance (baseline) between centers of the detection coil 22'-1 and the reference coil 23'-1 is 50 mm. The linear differential coil for measuring the magnetic field in the x direction is connected to an input coil of the SQUID through a superconducting wire on a mounting board in which a SQUID 21-1' is mounted and a biomagnetic field signal detected by the coil is supplied to the SQUID.

A sensor for measuring a magnetic field in the y direction includes a detection coil 22'-2 and a reference coil 23'-2 arranged side by side on one plane to form a linear differential coil for measuring the magnetic field in the y direction. The detection coil 22'-2 and the reference coil 23'-2 have a regular square of 20 mm×20 mm and a distance (baseline) between centers of the detection coil 22'-2 and the reference coil 23'-2 is 50 mm. The linear differential coil for measuring the magnetic field in the y direction is connected to an input coil of a SQUID through a superconducting wire on a mounting board in which a SQUID 21-2' is mounted and a magnetic field signal detected by the coil is supplied to the SQUID.

The magnetic sensors for detection of the x and y components are attached on two sides orthogonal to each other of a support in the form of a square pillar to form the magnetic sensor capable of measuring the x and y components of the biomagnetic field. The magnetic sensor formed into a square pillar as shown in FIG. 17 is arranged into a sensor array as shown in FIG. 2. The vector intensity I(x, y, t) and the angle θ (x, y, t) thereof are calculated from the measured tangential components $B_x$ and $B_y$ on the basis of the equations 3 and 4, respectively.

As described with reference to FIGS. 6 and 12, instead of calculation of a differentiation in the x and y directions of the normal component of the biomagnetic field, the vector intensity I(x, y, t) and the angle θ (x, y, t) thereof calculated from the two measured tangential components on the basis of the equations 3 and 4, respectively, can be used to calculate and display the time-intensity plot (t-$I_{max}$) and the time-angle plot (t-θ) of the maximum vector or the time-angle-intensity plot (t-θ·I) for all of 64 channels in the same manner as the first and second embodiments described above.

(Fourth Embodiment)

In the fourth embodiment, a planer type differential coil or gradiometer is used to directly measure and analyze linear differential components in the x and y directions of the normal component.

Figure 18:
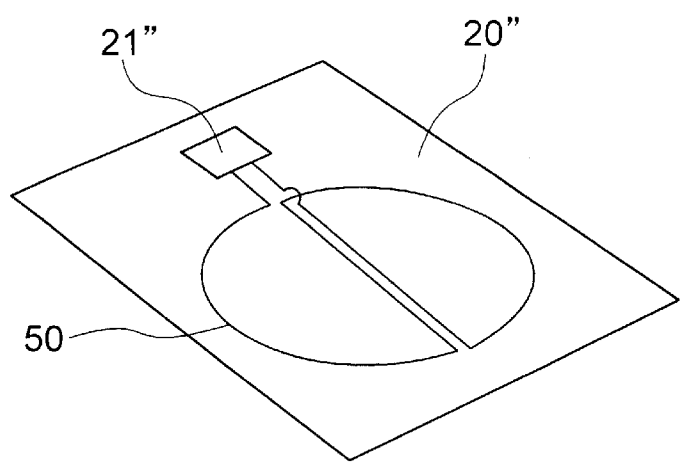
FIG. 18 is a diagram illustrating an example of a differential coil used in the fourth embodiment of the present invention and formed into a circle as a whole.

FIG. 18 is a diagram showing an example of a differential coil 50 used in the fourth embodiment of the present invention and formed into a circle as a whole including semi-circular coils arranged side by side and having straight portions in which currents opposite to each other flow when a magnetic field is coupled with the coils in the same direction. The planar type gradiometer 20" shown in FIG. 18 can detect a differentiated value of the magnetic field in the direction orthogonal to the straight portions in which the currents opposite to each other flow. The differential coil 50 is connected to the input coil of the SQUID through the superconducting wire on the mounting board in which the SQUID 21" is mounted and the biomagnetic field signal detected by the differential coil is supplied to the SQUID. Planar type differential coils having the straight portions in which currents opposite to each other flow, in the x and y directions, respectively, are provided.

The planar type differential coil for detecting differential components in the x and y directions can be disposed one over the other at each of measurement points of the sensor array as shown in FIG. 2 to thereby directly measure differential values in the x and y directions of the normal component of the biomagnetic field at each of 64 measurement points. The vector intensity I(x, y, t) and the angle θ (x, y, t) thereof are calculated from the measured differential values in the x and y directions on the basis of the equations 1 and 2, respectively. In the same manner as the first to third embodiments described above, the time-intensity plot (t-I$_{max}$) and the time-angle plot (t-θ) of the maximum vector or the time-angle·intensity plot (t-θ·I) for all of 64 channels can be calculated and displayed.

(Fifth Embodiment)

Figure 19:
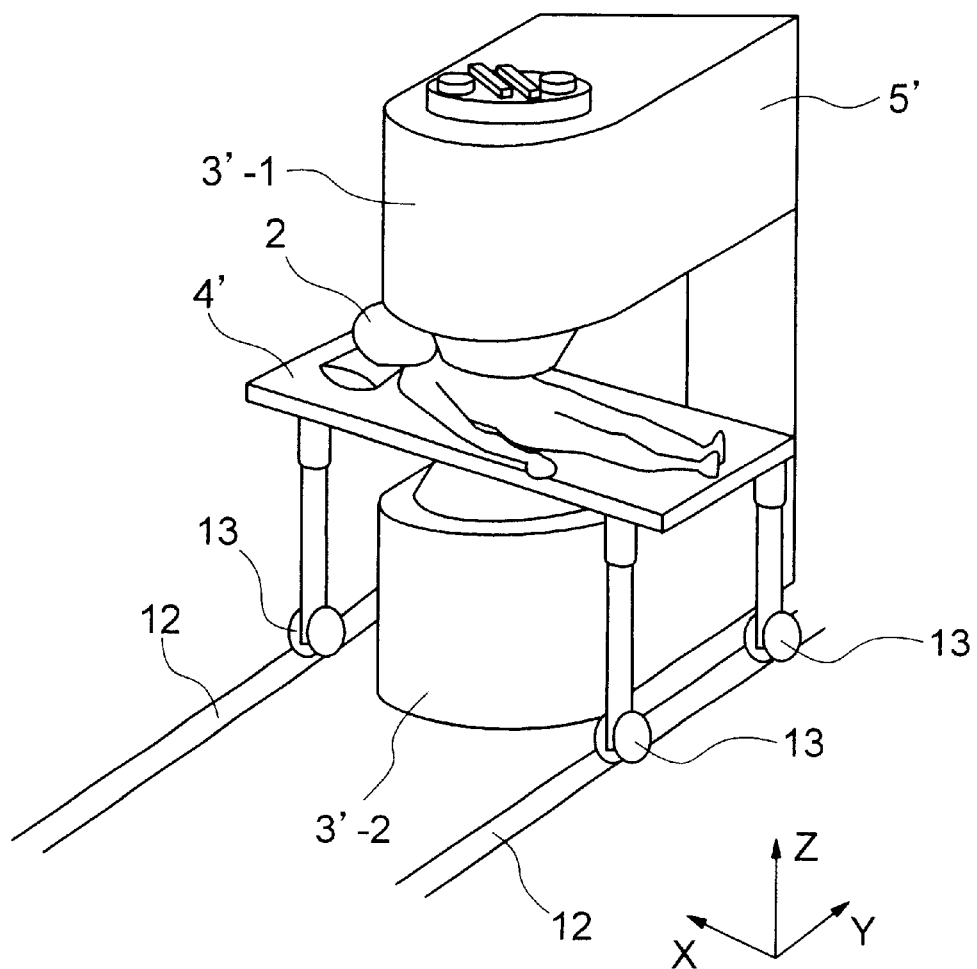
FIG. 19 is a diagram schematically illustrating an example of a biomagnetic field measuring apparatus used in a fifth embodiment of the present invention for performing cardiac magnetic field measurement on the front and the back simultaneously.

FIG. 19 is a diagram schematically illustrating an example of a biomagnetic field measuring apparatus used in the fifth embodiment of the present invention for performing cardiac magnetic field measurement on the front and the back simultaneously. In the biomagnetic field measuring apparatus of the fifth embodiment, the subject 2 is not required to change the posture thereof in order to measure the cardiac magnetic field on the front and the back and the biomagnetic field measuring apparatus can measure the cardiac magnetic field in the two direction simultaneously at a time. The measuring apparatus comprises two dewars including an upper dewar 3'-1 and a lower dewar 3'-2 each having any sensor array arranged therein as described in the first to fourth embodiments. The upper and lower dewars 3'-1 and 3'-2 are supported to a gantry 5'. Horizontally movable pulleys 13 are attached to legs of a bed 4'. After the subject 2 gets on the bed 4', the bed 4' is moved to a predetermined position between the upper and lower dewars 3'-1 and 3'-2 along rails 12. Since the cardiac magnetic field can be measured simultaneously in the two directions by means of the sensor array disposed above and under the subject 2 without measuring periodic living-body signals such as electrocardiogram, it is not necessary to adjust the time axis of cardiac magnetic field data measured in the two directions.

(Sixth Embodiment)

Figure 20:
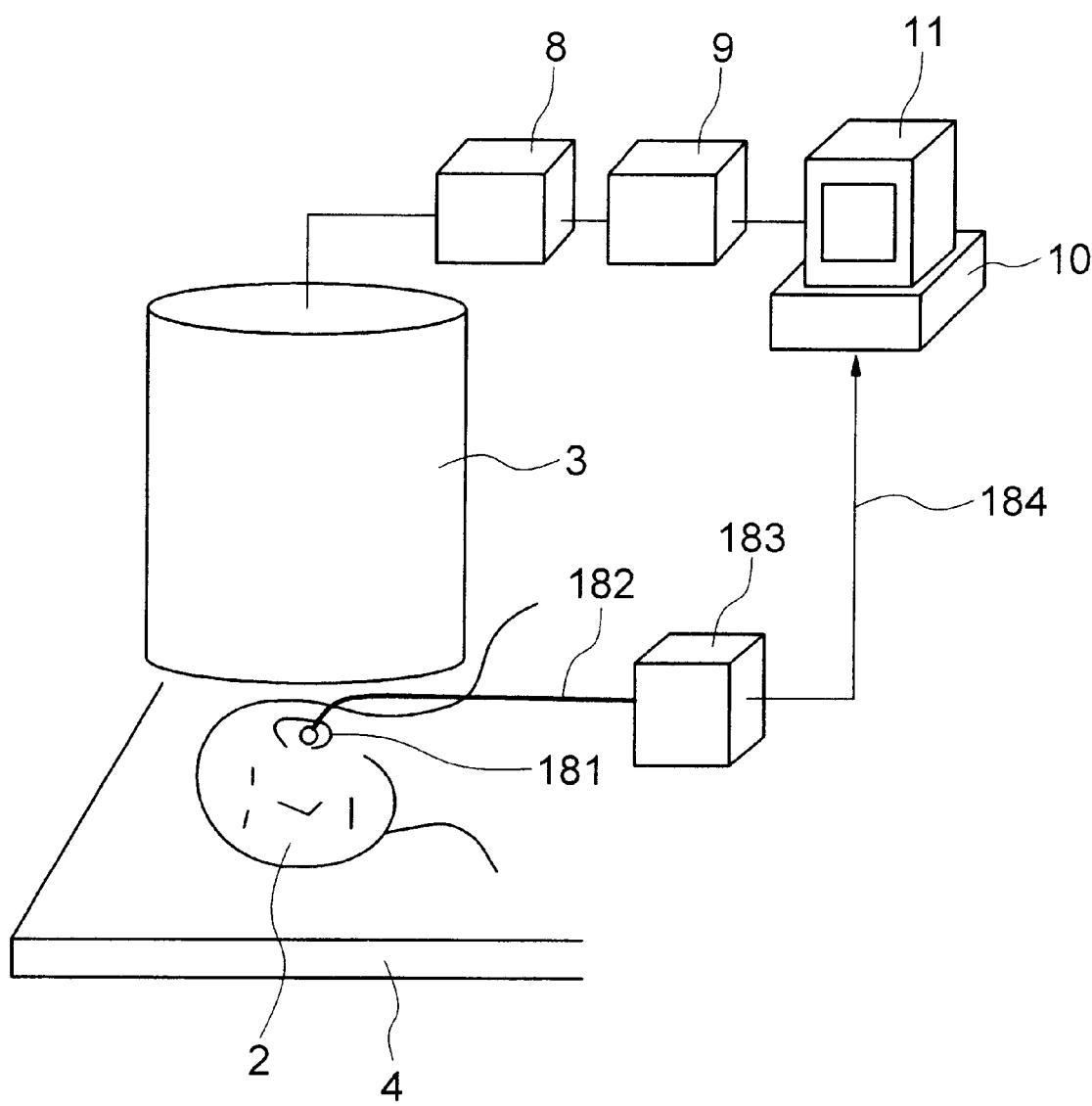
FIG. 20 is a perspective view schematically illustrating an example of a biomagnetic field measuring apparatus for measuring the auditory evoked cerebral magnetic field in a sixth embodiment of the present invention.

In the sixth embodiment, auditory evoked magnetic field (cerebral magnetic field) is measured. FIG. 20 is a perspective view schematically illustrating an example of a biomagnetic field measuring apparatus for measuring the auditory evoked magnetic field in the sixth embodiment of the present invention. The subject lies down on the bed 4 and brings the surface of the head to be measured near to the bottom of the dewar 3 to thereby measure the cerebral magnetic field.

In the structure shown in FIG. 20, a tone burst having a holding time width of 50 ms at 1 kHz is produced by an auditory stimulator 183. An interval of auditory stimulation is 0.3 Hz (a frequency of once per about 3.3 seconds). A synchronous signal 184 is produced in synchronism with a timing of application of the auditory stimulation to be supplied to the data acquisition and analysis apparatus (operation processing apparatus) 10. After the apparatus adjusts the time axes of waveforms of the cerebral magnetic field to coincide with one another by utilizing the synchronous signal 184 supplied thereto, the apparatus performs adding and averaging processing to improve a signal-to-noise ratio.

The tone burst produced by the auditory stimulator 184 is inputted to the left ear through an air tube 182 and an adapter 181. Although not shown in FIG. 20, measurement is performed so that there is no influence due to external sound while sound of white noise is always inputted to the right ear. The cerebral magnetic field is measured by the magnetic sensors in the dewar 3. The magnetic sensors are driven by an FLL circuit 8 and an output of the FLL circuit 8 is collected and recorded as digital data in the data acquisition and analysis apparatus 10 through the amplifier-filter circuit 9. A picture for controlling the data acquisition and analysis apparatus 10, the FLL circuit 8, the amplifier-filter circuit 9 and the like and a picture for displaying a result of data analysis are displayed in the display 11. It is desirable that constituent elements other than the bed 4 and the dewar 3 shown in FIG. 20 are disposed outside of the magnetically shielded room 1 shown in FIG. 1.

Figure 21:
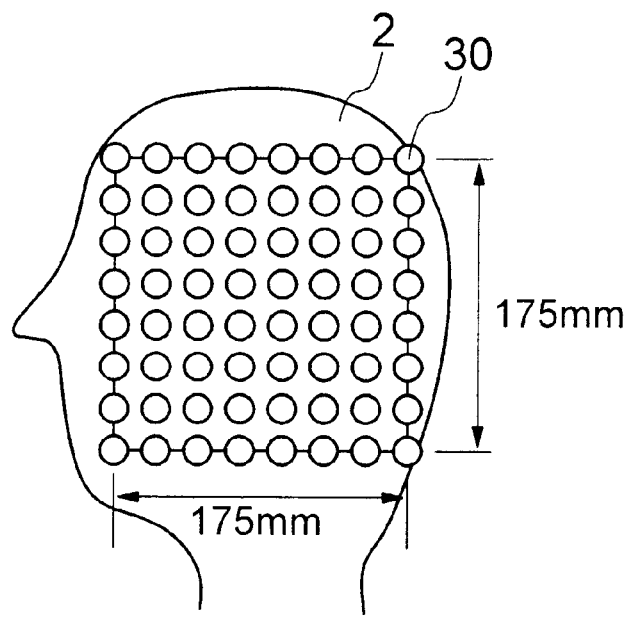
FIG. 21 is a diagram for explaining a positional relation of an arrangement of the magnetic sensors and the head of the human body in the sixth embodiment of the present invention.
Figure 21:
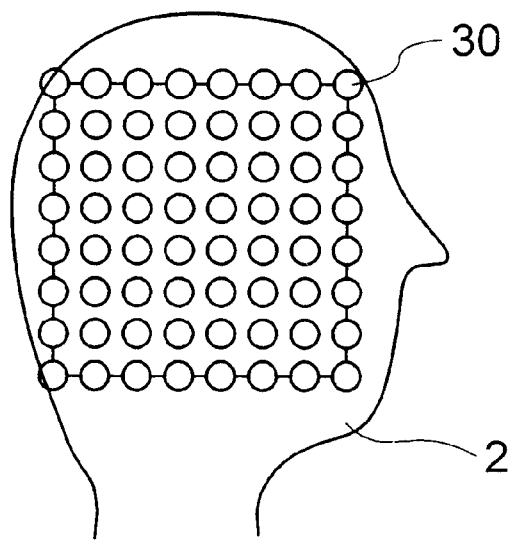

FIG. 21 is a diagram for explaining an arrangement of the magnetic sensors and the head of the human body in the sixth embodiment of the present invention. In FIG. 21, a measurement area (175 mm×175 mm) of the cerebral magnetic field is shown by measurement points 30 where the magnetic sensors are arranged. The measurement area for measuring the cerebral magnetic field from the left temporal side of the subject 2 is shown in the upper portion and the measurement area for measuring the cerebral magnetic field from the right temporal side thereof is shown in the lower portion of FIG. 21. In FIG. 21, since the auditory evoked magnetic field is measured, the measurement points 30 are also disposed at a slightly upper portion of the ear.

Figure 22:
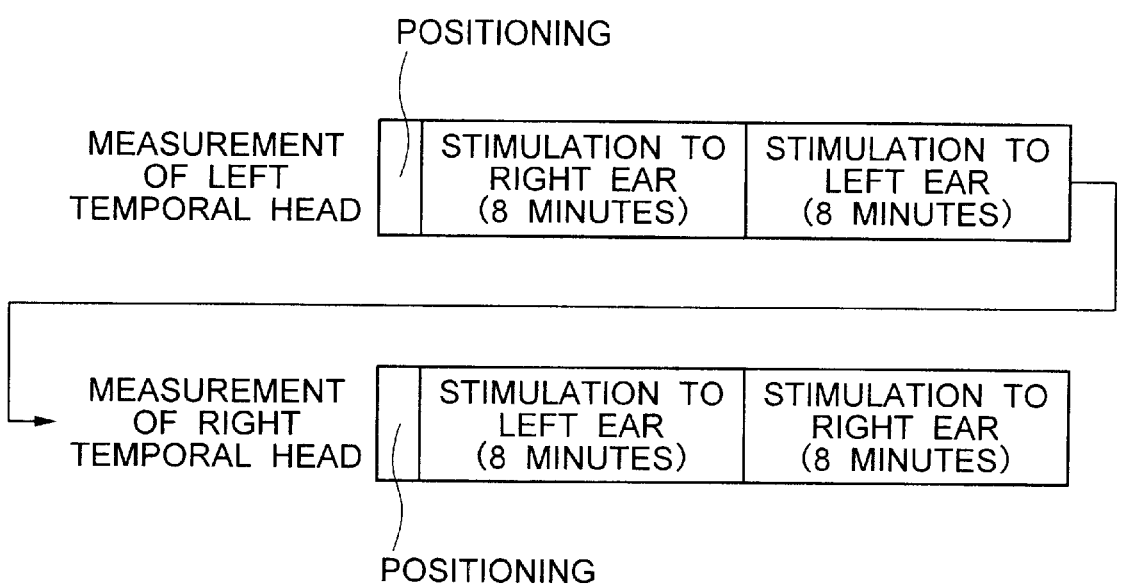
FIG. 22 is a flow chart for explaining measurement procedure of the cerebral magnetic field in the sixth embodiment of the present invention.

FIG. 22 is a flow chart for explaining measurement procedure of the cerebral magnetic field in the sixth embodiment of the present invention. Since the cerebral magnetic field is first measured from the left temporal head, the head of the subject 2 and the dewar 3 are positioned and the right ear is first stimulated for eight minutes (auditory stimulation to the opposite side). Then, the left ear is stimulated successively for eight minutes (auditory stimulation to the same side). In order to measure the cerebral magnetic field from the right temporal head successively, the subject 2 lies down on the bed 4 with the left shoulder downward and the positioning is performed. After completion of the positioning, the left ear is stimulated for eight minutes (auditory stimulation to the opposite side) and successively the right ear is stimulated for eight minutes (auditory stimulation to the same side).

Figure 23:
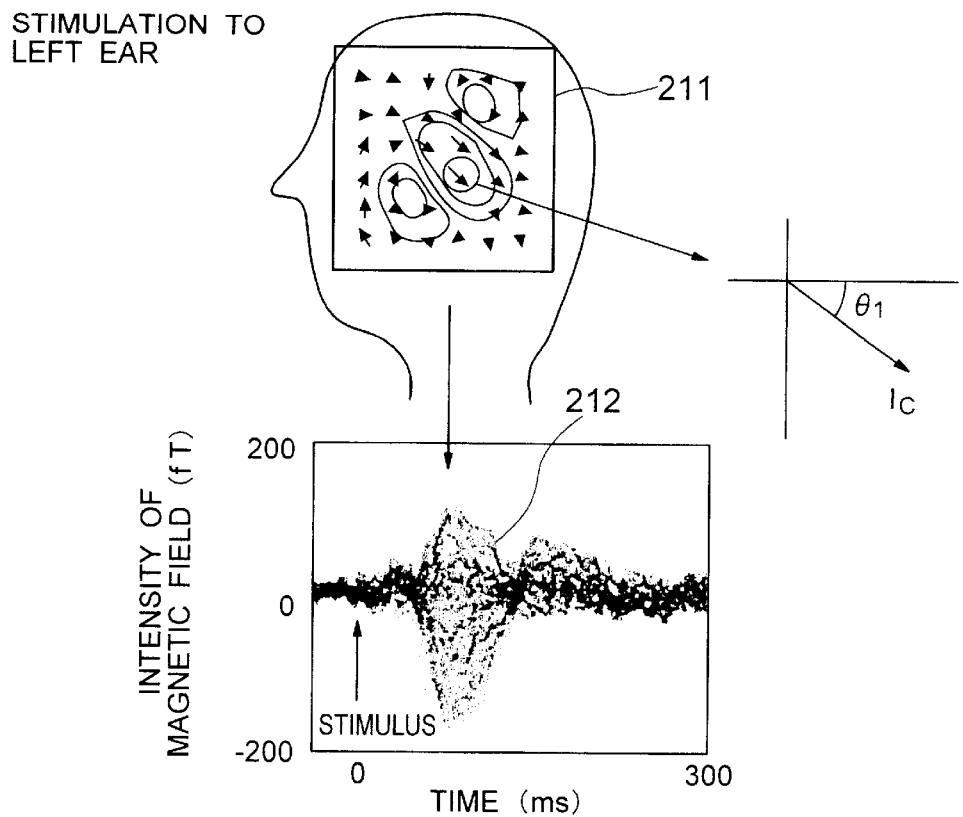
FIG. 23 is a diagram showing a display example of measured results of cerebral magnetic fields of the normal subject and the principle for extracting a maximum vector in the sixth embodiment of the present invention.
Figure 23:
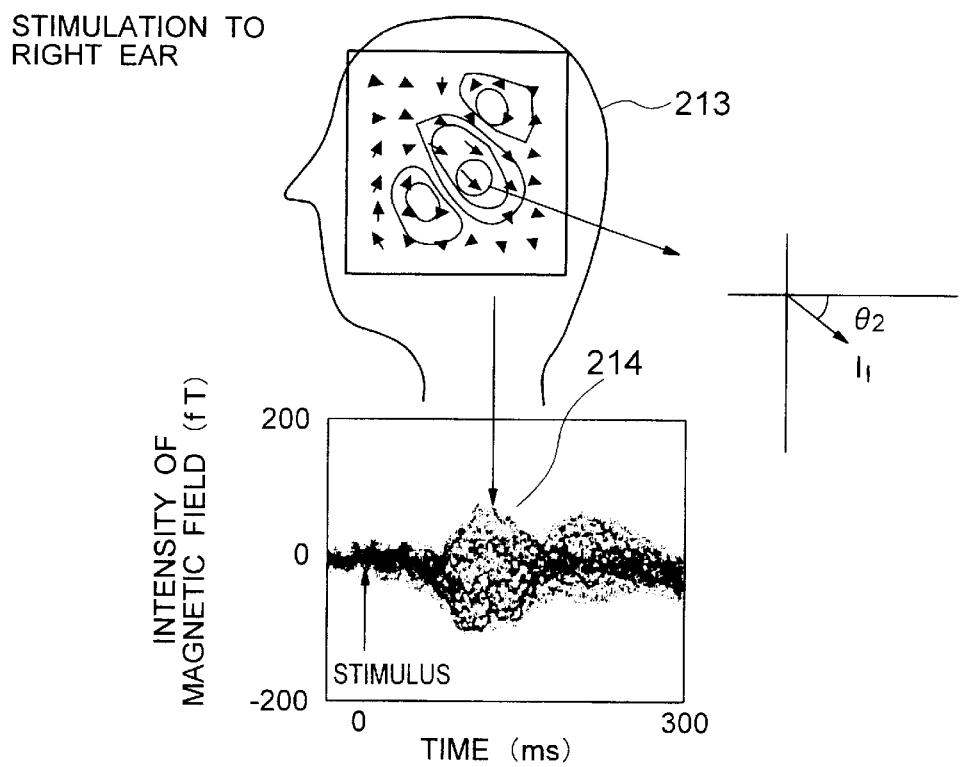

FIG. 23 is a diagram showing a display example of measured results of cerebral magnetic field of the normal subject and the principle for extracting a maximum vector in the sixth embodiment of the present invention. The measured result of the cerebral magnetic field in case where the left ear is stimulated is shown in the upper portion and the measured result of the cerebral magnetic field in case where the right ear is stimulated is shown in the lower portion of FIG. 23. Waveforms 212 and 214 of the cerebral magnetic field measured are displayed by overlapping waveforms of the cerebral magnetic field measured by all of 64 channels one over another and subjected to correction of the baseline in the time zone before the auditory stimulation, after averaging process has been performed 70 times.

Current arrow maps 211 and 213 indicate current arrow maps at the time that maximum peaks of the waveforms 212 and 214 of the measured cerebral magnetic field appear (the peaks are named N100m). An intensity $I_{CONTRALATERAL}$ (intensity of contralateral stimulus) (hereinafter referred to as $I_c$) and an inclination θ1 of a maximum current arrow are calculated from the maximum current arrow in the current arrow map 211. Similarly, an intensity $I_{IPSILATERAL}$ (intensity of ipsilateral stimulus) (hereinafter referred to as $I_i$) and an inclination θ2 of the maximum current arrow are calculated from the maximum current arrow in the current arrow map 213. An intensity ratio $I_i/I_c$ of the maximum current arrows (intensity of the ipsilateral stimulus/intensity of the contralateral stimulus) and a angle difference |Δθ|= |θ1−θ2| are calculated. Even when the cerebral magnetic field is measured from the right temporal head, $I_c$ (intensity of contralateral stimulus) uses the maximum current arrow upon the peak of the waveform of the cerebral magnetic field by stimulation to the left ear and $I_i$ (intensity of ipsilateral stimulus) uses the maximum current arrow upon the peak of the waveform of the cerebral magnetic field by stimulation to the right ear.

Figure 24:
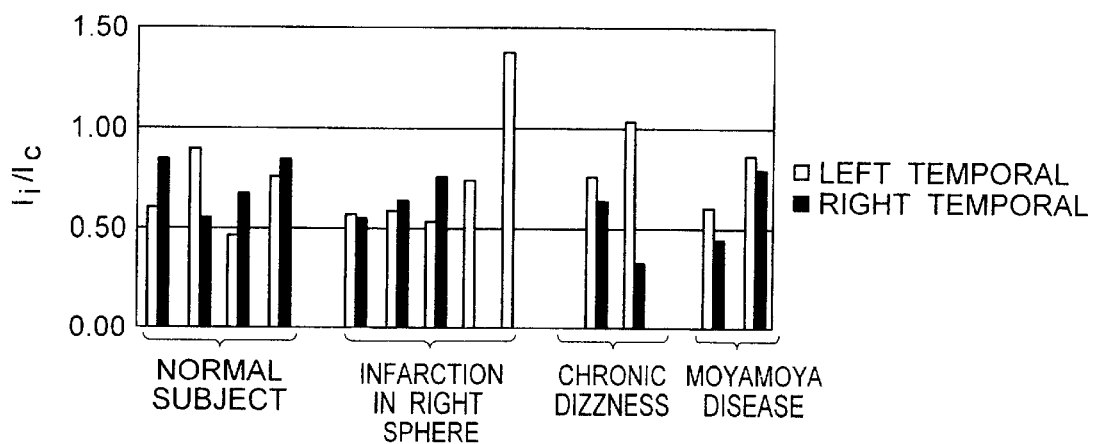
FIG. 24 is a diagram showing an example of the result of the intensity ratio $I_i/I_c$ (intensity of the ipsilateral stimulus/intensity of the contralateral stimulus) of the maximum current vector obtained in the sixth embodiment of the present invention.

FIG. 24 is a diagram showing an example of the result of the intensity ratio $I_i/I_c$ (intensity of the ipsilateral stimulus/ intensity of the contralateral stimulus) of the maximum current vector obtained in the sixth embodiment of the present invention.

Figure 25:
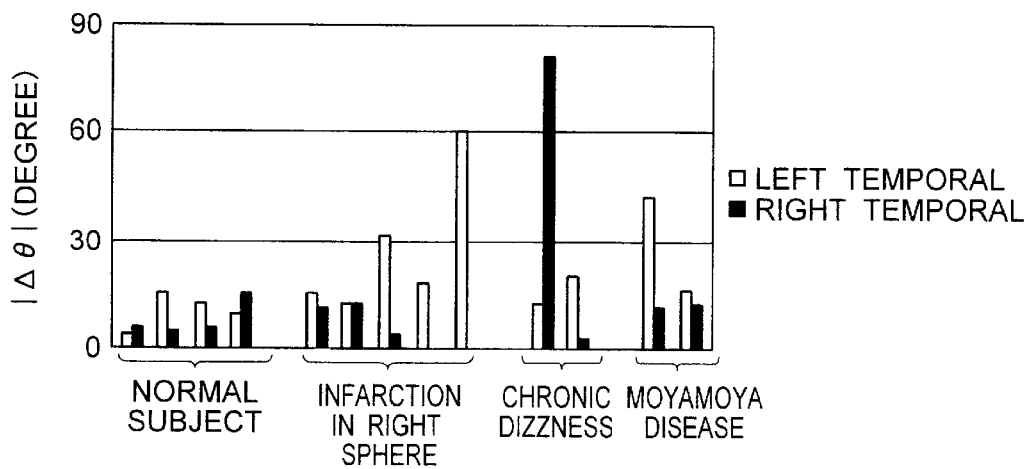
FIG. 25 is a diagram showing an example of the result of the angle difference $|\Delta\theta|$ obtained in the sixth embodiment of the present invention.

FIG. 25 is a diagram showing an example of the result of the angle difference $|\Delta\theta|$ obtained in the sixth embodiment of the present invention.

Figure 26:
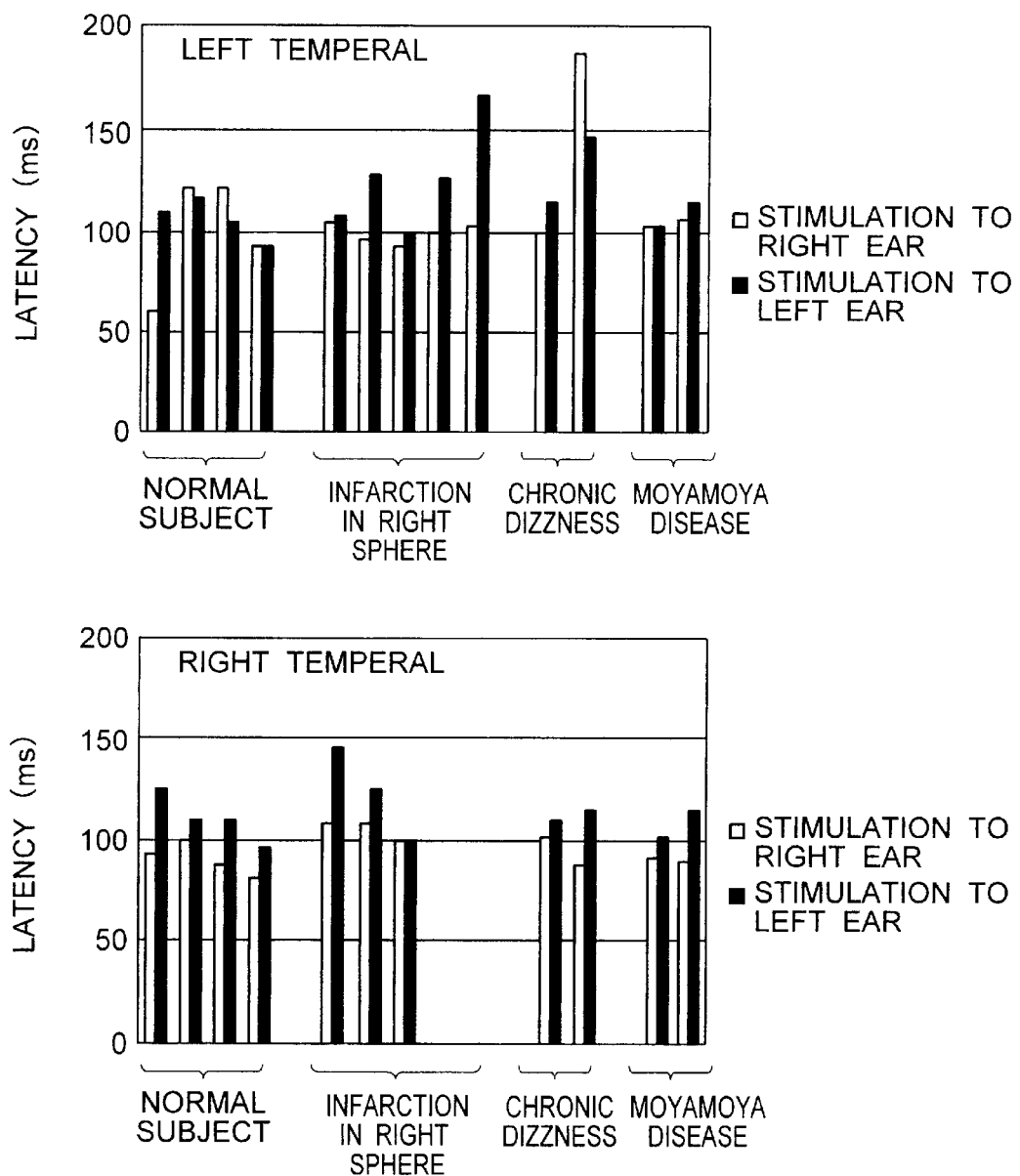
FIG. 26 is a diagram showing an example of the results arranged for each temporal, of time (latency) that N100m obtained in the sixth embodiment of the present invention appears.

FIG. 26 is a diagram showing an example of the results arranged for each temporal, of time (latency) that the N100m obtained in the sixth embodiment of the present invention appears.

Referring to FIGS. 24 to 26, four examples of the normal subjects, five examples of patients having infarction in the right hemisphere, two examples of patients having chronic dizziness, and two examples of patients having moyamoya disease that trouble is observed in cerebral blood flow are described. However, in two examples of five patients having the infarction in the right hemisphere, any cerebral magnetic field waveform is not detected in the right temporal head since the infarction area is spread widely.

As shown in FIG. 24, it is understood that a current ratio is smaller than 1 in both temporal heads of the normal subject and the current arrow intensity on the contralateral side of the normal subject is strong. On the other hand, it is understood that there is a case where the current ratio is larger than 1 in one example of the patient having the infarction in the right hemisphere (right-side infarction) and one example of the patient having the moyamoya disease. In two examples of the patients having the moyamoya disease, the current ratio is smaller than 1 in the same way as the normal subject.

As shown in FIG. 25, it is understood that the angle difference in both the temporal heads of the normal subject is smaller than 20 degrees and the directions of the maximum vectors are identical considerably in the normal subject. On the other hand, in three of the six examples of the patients having the right side infarction, the angle difference exceeding 20 degrees is observed and even in one example of the patient having the chronic dizziness and in one example of the patient having the moyamoya disease, the result that the angle difference is greatly different from other cases is obtained.

As shown in FIG. 26, in the right temporal head of the normal subject, the latency of the auditory stimulation to the contralateral side (stimulation to the left ear) is significantly short as a result, while any significance is not recognized in the left temporal head particularly. There is observed the result that in the left temporal head having the right hemisphere infarction, the latency is prolonged by the auditory stimulation to the ipsilateral side (stimulation to the left ear) in three of the six examples as compared with the normal subject. It is understood that there appears the tendency that the auditory stimulation to the contralateral side (stimulation to the right ear) is prolonged in the right temporal head having the right hemisphere infarction as compared with the normal subject and even the auditory stimulation to the ipsilateral side (stimulation to the right ear) is prolonged in one of the three examples.

In the patient having the chronic dizziness, there was obtained the result that the latency for the left temporal head is prolonged in one of two examples. On the other hand, in the patient having the moyamoya disease, any significant difference from the normal subject is not recognized in the latency in both the temporal heads Although detailed explanation is omitted, the synchronous signals synchronizing with the start of application of the stimulation signal such as light and sound applied to the living body are collected as pairs with the cerebral magnetic field signals and conversion of time axis, that is, conversion for moving the time axis in parallel is performed so that the time axis of waveforms of the cerebral magnetic field measured in a plurality of directions has a common origin (t=0) at the time that the synchronous signals are collected. Next, in the same manner as the first to fourth embodiments, the vector intensity I(x, y, t) and the angle θ (x, y, t) thereof are calculated and the time-intensity plot (t-$I_{max}$) and the time-angle plot (t-θ) of the maximum vector or the time-angle·intensity plot (t-θ·I) for all of the channels is calculated and displayed.

In the embodiments of the present invention described above, since the vector intensity and the angle thereof obtained from the measured magnetic field waveforms of the cardiac or cerebral magnetic field are used, it is not necessary to analyze the phenomena in the living body by means of a lot of maps representing states at individual times in parts of the living body as in the prior art and the change in time of the electro-physiological excitation of the living body in the heart and the brain can be grasped in detail by means of an extremely smaller number of maps than the number of maps used in the prior art.

What is claimed is:

1. A biomagnetic field measuring apparatus comprising:
   a plurality of SQUID magneto-meters arranged in parallel on a x-y plane parallel to a surface of a living body for measuring a biomagnetic field generated from the living body to provide a plurality of biomagnetic field signals;
   a living-body signal measuring device for measuring and collecting living-body signals generated periodically other than the biomagnetic field signals;
   an operation processing device for operation-processing said biomagnetic field signals and said living-body signals measured simultaneously as pairs in a plurality of directions; and
   a display unit for displaying an output from said operation processing device,
   wherein said operation processing device synchronizes said biomagnetic field signals measured at different time points and in the plurality of directions into biomagnetic field data recorded in SQUID positional variables x, y, and a time variable t by using said living-body signals measured in the plurality of directions, calculates at least one of an intensity and an angle of each of said biomagnetic field signals based upon said biomagnetic field data, and
   wherein said display unit displays changes in time of said at least one of an intensity and an angle of each of said biomagnetic field signals measured by all of the SQUID magneto-meters on one display screen.

2. A biomagnetic field measuring apparatus according to claim 1, wherein said operation processing device calculates one maximum intensity among intensities of said biomagnetic field signals and a corresponding angle for individual time points represented by the time variable t, and said display unit displays changes in time of at least one of the maximum intensity and the corresponding angle.

3. A biomagnetic field measuring apparatus according to claim 2, wherein the changes in time of said at least one of the maximum intensity and the corresponding angle is displayed in said display unit by means of the same time axis in said respective directions in which said biomagnetic field is measured.

4. A biomagnetic field measuring apparatus according to claim 2, wherein the changes in time of said at least one of the maximum intensity and the corresponding angle is displayed in said display unit by means of the same time axis and in different colors in said respective directions in which said biomagnetic field is measured.

5. A biomagnetic field measuring apparatus according to claim 1, wherein said display unit displays the changes in time of said at least one of an intensity and an angle of each of said magnetic fields while proportionating intensities of said magnetic fields to a size of plotted points or distinguishing the intensities by different colors.

6. A biomagnetic field measuring apparatus comprising:
a plurality of SQUID magneto-meters arranged in parallel on a x-y plane parallel to a surface of a living body for measuring a biomagnetic field generated from the living body to provide a plurality of biomagnetic field signals;
a device for measuring one set of waveforms in electrocardiogram, waveforms in heart sound, and waveforms in polygraph as a living-body signal;
an operation processing device for operation processing said biomagnetic field signals and said living-body signals measured simultaneously as pairs in two directions on a breast side and a back side of the living body; and
a display unit for displaying an output from said operation processing device,
wherein said operation processing device synchronizes said biomagnetic field signals measured at different time points and in the plurality of directions into biomagnetic field data recorded in SQUID positional variables x, y, and a time variable t by using waveforms measured by the measuring device, calculates at least one of an intensity and an angle of each of said biomagnetic field signals based upon said biomagnetic field data, and
wherein said display unit displays changes in time of at least one of a maximum intensity and a corresponding angle of said biomagnetic field signals.

7. A biomagnetic field measuring apparatus according to claim 6, wherein a left horizontal direction vertical to a body axis of the living body is set to define an angle 0°, and said display unit displays in angle ranges of 0° to 180° and 0° to −180°.

8. A biomagnetic field measuring apparatus comprising:
a plurality of SQUID magneto-meters arranged in parallel on a x-y plane parallel to a surface of a living body for measuring a biomagnetic field generated from a heart or a brain of the living body in a plurality of directions to provide a plurality of biomagnetic field signals;
an operation processing device for operation processing said biomagnetic field signals; and
a display unit for displaying an output from said operation processing device,
wherein said operation processing device calculates one maximum intensity among intensities of said biomagnetic field signals and a corresponding angle for individual time points represented by a time variable t, and
wherein said display unit displays changes in time of at least one of the maximum intensity and the corresponding angle.

9. A biomagnetic field measuring apparatus comprising:
a plurality of SQUID magneto-meters arranged in parallel on a x-y plane parallel to a surface of a living body for measuring a biomagnetic field generated from a heart or a brain of the living body in a plurality of directions to provide a plurality of biomagnetic field signals;
an operation processing device for operation processing said biomagnetic field signals; and
a display unit for displaying an output from said operation processing device,
wherein said operation processing device calculates at least one of an intensity and an angle of each of said biomagnetic field signals based upon said biomagnetic field signals, and
wherein said display unit displays changes in time of said at least one of an intensity and an angle of each of said biomagnetic field signals measured by all of the SQUID magneto-meters on one display screen, while proportionating intensities of said biomagnetic field signals to a size of plotted points or distinguishing the intensities by different colors.

10. A biomagnetic field measuring apparatus comprising:
a plurality of SQUID magneto-meters arranged in parallel on a x-y plane parallel to a surface of a living body for measuring a biomagnetic field generated from a brain of the living body to provide a plurality of biomagnetic field signals;
a stimulator for generating stimulation signals for stimulating the living body and synchronous signals each synchronizing with the start of one of said stimulation signals;
an operation processing device for operation processing said biomagnetic field signals and said synchronous signals measured as pairs in a plurality of directions in the brain of the living body; and
a display unit for displaying an output from said operation processing device,
wherein said operation processing device synchronizes said biomagnetic field signals measured at different time points and in the plurality of directions into biomagnetic field data recorded in SQUID positional variables x, y, and a time variable t on the basis of said synchronous signals, and calculates at least one of an intensity and an angle of each of said biomagnetic field signals based upon said biomagnetic field data, and
wherein said display unit displays changes in time of said at least one of an intensity and an angle of each of said biomagnetic field signals measured by all of the SQUID magneto-meters on one display screen.

11. A biomagnetic field measuring apparatus comprising:
a plurality of SQUID magneto-meters arranged in parallel on a x-y plane parallel to a surface of a living body for measuring a biomagnetic field generated from a brain of the living body to provide a plurality of biomagnetic field signals;
a stimulator for generating stimulation signals for stimulating the living body and synchronous signals each synchronizing with the start of one of said stimulation signals;
an operation processing device for operation processing said biomagnetic field signals and said synchronous signals measured as pairs in a plurality of directions in the brain of the living body; and
a display unit for displaying an output from said operation processing device, wherein said operation processing device synchronizes said biomagnetic field signals measured at different time points and in the plurality of directions into biomagnetic field data recorded in SQUID positional variables x, y, and a time variable t on the basis of said synchronous signals, and calculates one maximum intensity among intensities of said biomagnetic field signals and a corresponding angle for individual time points represented by a time variable t, and wherein said display unit displays changes in time of at least one of the maximum intensity and the corresponding angle.

* * * * *